United States Patent
Tom et al.

(10) Patent No.: US 10,646,519 B2
(45) Date of Patent: May 12, 2020

(54) METHODS OF MANUFACTURE OF THERAPEUTIC PRODUCTS COMPRISING VITALIZED PLACENTAL DISPERSIONS

(71) Applicant: Osiris Therapeutics, Inc., Columbia, MD (US)

(72) Inventors: Samson Tom, Baltimore, MD (US); Alla Danilkovitch, Columbia, MD (US); Dana Yoo, Falls Church, VA (US); Timothy Jansen, Baltimore, MD (US); Jin-Qiang Kuang, Woodstock, MD (US); Jennifer Michelle Marconi, Glen Burnie, MD (US)

(73) Assignee: Osiris Therapeutics, Inc., Columbia, MD (US)

( * ) Notice: Subject to any disclaimer, the term of this patent is extended or adjusted under 35 U.S.C. 154(b) by 71 days.

(21) Appl. No.: 15/949,808

(22) Filed: Apr. 10, 2018

(65) Prior Publication Data

US 2018/0360886 A1 Dec. 20, 2018

Related U.S. Application Data

(63) Continuation of application No. 14/070,040, filed on Nov. 1, 2013, now Pat. No. 9,956,248, which is a continuation of application No. 13/030,595, filed on Feb. 18, 2011, now abandoned.

(60) Provisional application No. 61/369,562, filed on Jul. 30, 2010, provisional application No. 61/338,464, filed on Feb. 18, 2010, provisional application No. 61/338,489, filed on Feb. 18, 2010.

(51) Int. Cl.
| | |
|---|---|
| *A61K 35/28* | (2015.01) |
| *A61K 35/50* | (2015.01) |
| *A01N 1/02* | (2006.01) |
| *A61K 38/18* | (2006.01) |
| *A61K 38/19* | (2006.01) |
| *A61K 38/57* | (2006.01) |
| *C12N 5/073* | (2010.01) |
| *A61K 38/39* | (2006.01) |

(52) U.S. Cl.
CPC ............ *A61K 35/28* (2013.01); *A01N 1/0221* (2013.01); *A61K 35/50* (2013.01); *A61K 38/1825* (2013.01); *A61K 38/1841* (2013.01); *A61K 38/39* (2013.01); *A61K 38/57* (2013.01); *C12N 5/0605* (2013.01); *C12N 2500/02* (2013.01); *C12N 2501/115* (2013.01); *C12N 2502/025* (2013.01)

(58) Field of Classification Search
None
See application file for complete search history.

(56) References Cited

U.S. PATENT DOCUMENTS

| | | | |
|---|---|---|---|
| 5,891,617 A | 4/1999 | Watson et al. | |
| 6,152,142 A | 11/2000 | Tseng | |
| 6,326,019 B1 | 12/2001 | Tseng | |
| 8,071,135 B2 * | 12/2011 | Liu | A61K 35/44 424/583 |
| 8,460,715 B2 | 6/2013 | Daniel | |
| 8,932,641 B2 | 1/2015 | Nikaido et al. | |
| 10,272,116 B2 | 4/2019 | Tom et al. | |
| 2002/0039788 A1 | 4/2002 | Isseroff et al. | |
| 2003/0235563 A1 | 12/2003 | Strom et al. | |
| 2004/0048796 A1 | 3/2004 | Hariri et al. | |
| 2006/0003927 A1 | 1/2006 | Champion et al. | |
| 2006/0023376 A1 | 2/2006 | Gill | |
| 2006/0182724 A1 | 8/2006 | Riordan | |
| 2006/0228339 A1 | 10/2006 | Wang | |
| 2007/0015278 A1 | 1/2007 | Li et al. | |
| 2007/0041954 A1 | 2/2007 | Ichim | |
| 2007/0071740 A1 | 3/2007 | Tseng et al. | |
| 2007/0116684 A1 | 5/2007 | Atala et al. | |
| 2007/0134210 A1 | 6/2007 | Heidaran | |
| 2007/0134261 A1 | 6/2007 | Hancock et al. | |
| 2007/0178159 A1 | 8/2007 | Chen et al. | |
| 2007/0231297 A1 | 10/2007 | Smith et al. | |
| 2007/0275362 A1 | 11/2007 | Edinger et al. | |
| 2008/0044848 A1 | 2/2008 | Heidaran | |
| 2008/0046095 A1 | 2/2008 | Daniel | |

(Continued)

FOREIGN PATENT DOCUMENTS

| | | |
|---|---|---|
| AU | 2014393403 | 11/2016 |
| CA | 2790322 | 2/2011 |

(Continued)

OTHER PUBLICATIONS

Genbacev, Olga; et al; "Serum-free derivation of human embryonic stem cell lines on human placental fibroblast feeders" Fertility and Sterility, 83, 1517-1529, 2005 (Year: 2005).*

(Continued)

*Primary Examiner* — David W Berke-Schlessel

(74) *Attorney, Agent, or Firm* — Norton Rose Fulbright US LLP

(57) ABSTRACT

This invention provides a fluid therapeutic placental product comprising placental cells and a placental dispersion comprising placental factors. The placental cells and the placental dispersion are derived from placental tissue. A placental tissue can optionally be an amnion, chorion, or a trophoblast-depleted chorion. The placental product of the present invention is useful in treating a patient with a tissue injury (e.g. wound or burn) by applying the placental product to the injury. Similar application is useful with ligament and tendon repair and for engraftment procedures such as bone engraftment.

19 Claims, 14 Drawing Sheets

(56) References Cited

U.S. PATENT DOCUMENTS

| | | |
|---|---|---|
| 2008/0069895 A1 | 3/2008 | Liu et al. |
| 2008/0131522 A1 | 6/2008 | Liu et al. |
| 2008/0138396 A1 | 6/2008 | Low et al. |
| 2008/0145344 A1 | 6/2008 | Deshpande et al. |
| 2008/0152629 A1* | 6/2008 | Edinger ............... C12N 5/0605 424/93.7 |
| 2008/0175824 A1 | 7/2008 | Heidaran et al. |
| 2008/0181935 A1 | 7/2008 | Bhatia et al. |
| 2008/0193554 A1 | 8/2008 | Dua et al. |
| 2008/0213332 A1 | 9/2008 | Slavin et al. |
| 2008/0226595 A1 | 9/2008 | Edinger et al. |
| 2008/0299087 A1 | 12/2008 | Tseng et al. |
| 2009/0104164 A1 | 4/2009 | Zhang et al. |
| 2009/0169597 A1 | 7/2009 | Brown et al. |
| 2009/0252710 A1 | 10/2009 | Zhang et al. |
| 2010/0047351 A1 | 2/2010 | Zeitlin et al. |
| 2010/0098743 A1 | 4/2010 | Nikaido et al. |
| 2010/0119496 A1 | 5/2010 | Wilkison et al. |
| 2011/0206776 A1 | 8/2011 | Tom et al. |
| 2011/0251566 A1 | 10/2011 | Zimintsky et al. |
| 2012/0095455 A1 | 4/2012 | Rodmond et al. |
| 2014/0037598 A1 | 2/2014 | Jansen et al. |
| 2014/0160447 A1 | 6/2014 | Kobayashi et al. |

FOREIGN PATENT DOCUMENTS

| | | |
|---|---|---|
| CA | 2790325 | 2/2011 |
| CA | 2790333 | 2/2011 |
| CA | 2790336 | 2/2011 |
| CA | 2790340 | 2/2011 |
| CA | 2790436 | 2/2011 |
| CA | 2948129 | 11/2016 |
| EP | 2702871 A1 | 2/1955 |
| EP | 11745341.5 | 2/2011 |
| EP | 11745347.2 | 2/2011 |
| EP | 11745353.0 | 2/2011 |
| EP | 11745360.5 | 2/2011 |
| EP | 11745361.3 | 2/2011 |
| EP | 14891208.2 | 5/2014 |
| EP | 17205385.2 | 12/2017 |
| JP | 2016-566889 | 11/2016 |
| KR | 10-2016-7034113 | 12/2016 |
| SG | 11201609253 P | 11/2016 |
| WO | WO-98/37903 A1 | 9/1998 |
| WO | WO-2005/001076 A2 | 1/2005 |
| WO | WO-2005/007835 A1 | 1/2005 |
| WO | WO-2005/021014 A1 | 3/2005 |
| WO | WO-2006/071794 A2 | 7/2006 |
| WO | WO-2006/094247 A2 | 9/2006 |
| WO | WO-2007/023750 A1 | 3/2007 |
| WO | WO-2007/079183 A2 | 7/2007 |
| WO | WO-2007/079184 A2 | 7/2007 |
| WO | WO-2008/146991 A1 | 12/2008 |
| WO | WO-2008/151846 A2 | 12/2008 |
| WO | WO-2009/120996 A1 | 10/2009 |
| WO | WO-2009/132186 A1 | 10/2009 |
| WO | PCT/US2011/025459 | 2/2011 |
| WO | WO-2011/074208 A1 | 6/2011 |
| WO | PCT/US2014/037201 | 5/2014 |
| WO | PCT/US2014/037204 | 5/2014 |
| WO | PCT/US2014/037208 | 5/2014 |

OTHER PUBLICATIONS

Eldad, A; et al; "Amniotic membranes as a biological dressing" South African Medical Journal, 51, 272-275, 1977 (Year: 1977).*

Taylor, Pamela V; Hancock KW; "Antigenicity of Trophoblast and Possible Antigen-masking Effects during Pregnancy" Immunology, 28, 973-982, 1975 (Year: 1975).*

Li, H; et al; "Hypoxia-induced Increase in Soluble Flt-1 Production Correlates with Enhanced Oxidative Stress in Trophoblast Cells from the Human Placenta" Placenta, 26, 210-217, 2005 (Year: 2005).*

Dua, Harminder S; Azuara-Blanco, Augusto; "Amniotic membrane transplantation" British Journal of Ophthalmology, 83, 748-752, 1999 (Year: 1999).*

Meller, D. et al., Amniotic Membrane Transplantation in the Human Eye. Dtsch Arztebl Int. 2011; 108(14):243-8.

Rama, P. et al., Further Evaluation of Amniotic Membrane Banking for Transplantation in Ocular Surface Diseases. Cell Tissue Bank. 2001; 2(3):155-63.

Thomasen, H. et al., Comparison of Cryopreserved and Air-dried Human Amniotic Membrane for Opthalmologic Applications. Graefes Arch Clin Exp Opthalmol. 2009; 247(12):1691-700.

Communication Pursuant to Article 94(3) EPC dated Jun. 13, 2018 by the European Patent Office for Patent Application No. 14891208. 2, which was filed on May 7, 2014 and published as EP 3139934 on Mar. 15, 2017 (Inventor—Tom et al.; Applicant—Osiris Therapeutics, Inc.) (4 pages).

Office Action dated May 22, 2018 by the Japanese Patent Office for Patent Application No. 2016-566889, which was filed on Nov. 7, 2016 (Inventor—Tom et al.; Applicant—Osiris Therapeutics, Inc.) (Original—4 pages; Translation—5 pages).

Communication Pursuant to Article 94(3) EPC dated Jun. 29, 2018 by the European Patent Office for Patent Application No. 11745347. 2, which was filed on Feb. 18, 2011 and published as EP 2536825 on Dec. 26, 2012 (Inventor—Tom et al.; Applicant—Osiris Therapeutics, Inc.) (4 pages).

Communication Pursuant to Article 94(3) EPC dated Jun. 15, 2018 by the European Patent Office for Patent Application No. 14891554. 9, which was filed on May 7, 2014 and published as EP 3139936 on Mar. 15, 2017 (Inventor—Tom et al.; Applicant—Osiris Therapeutics, Inc.) (7 pages).

Communication Pursuant to Article 94(3) EPC dated Jul. 24, 2018 by the European Patent Office for Patent Application No. 11745360. 5, which was filed on Feb. 18, 2011 and published as EP 2536826 on Dec. 26, 2012 (Inventor—Jansen et al.; Applicant—Osiris Therapeutics, Inc.) (5 pages).

Communication Pursuant to Article 94(3) EPC dated Jul. 2, 2018 by the European Patent Office for Patent Application No. 14891336.1, which was filed on May 7, 2014 and published as EP 3139935 on Mar. 15, 2017 (Inventor—Jansen et al.; Applicant—Osiris Therapeutics, Inc.) (5 pages).

Final Office Action dated Jul. 26, 2018 by the U.S. Patent and Trademark Office for U.S. Appl. No. 14/172,940, filed Feb. 5, 2014 and published as US 2014/0294777 on Oct. 2, 2014 (Inventor—Tom et al.; Applicant—Osiris Therapeutics, Inc.) (20 pages).

Final Office Action dated Aug. 14, 2018 by the U.S. Patent and Trademark Office for U.S. Appl. No. 14/070,035, filed Nov. 1, 2013 and published as US 2014/0127317 on May 8, 2014 (Inventor—Jansen et al.; Applicant—Osiris Therapeutics, Inc.) (22 pages).

Office Action dated Feb. 4, 2019 by the Canadian Intellectual Property Office for Patent Application No. 2,790,333, which was filed on Aug. 17, 2012 (Inventor—Jansen et al.; Applicant—Osiris Therapeutics, Inc.) (4 pages).

Final Office Action dated Feb. 5, 2019 by the U.S. Patent and Trademark Office for U.S. Appl. No. 14/056,101, filed Oct. 17, 2013 and published as US 2014/0037598 on Feb. 6, 2014 (Inventor—Jansen et al.; Applicant—Osiris Therapeutics, Inc.) (14 pages).

Final Office Action dated Sep. 20, 2018 by the U.S. Patent and Trademark Office for U.S. Appl. No. 14/291,256, filed May 30, 2014 and published as US 2014/0301986 on Oct. 9, 2014 (Inventor—Tom et al.; Applicant—Osiris Therapeutics, Inc.) (26 pages).

Notice of Reason for Rejection dated Oct. 9, 2018 by the Intellectual Property Office of Japan for Patent Application No. 2016-567041, which was filed on Nov. 7, 2016 (Inventor—Tom et al.; Applicant—Osiris Therapeutics, Inc.) (Original—2 pages; Translation—2 pages).

Office Action dated Oct. 3, 2018 by the Canadian Intellectual Property Office for Patent Application No. 2,790,336, which was filed on Aug. 17, 2012 (Inventor—Jansen et al.; Applicant—Osiris Therapeutics, Inc.) (5 pages).

Notice of Reasons for Rejection dated Nov. 6, 2018 by the Intellectual Property Office of Japan for Patent Application No. 2016-566997, which was filed on Nov. 7, 2016 (Inventor—Jansen et al.; Applicant—Osiris Therapeutics, Inc.) (Original—3 pages; Translation—3 pages).

(56) References Cited

OTHER PUBLICATIONS

Adds et al., Amniotic membrane grafts, "fresh" or frozen? A clinical and in vitro comparison. Br J Ophthalmol. 2001; 85(8):905-7.
Aggarwal et al., Human mesenchymal stem cells modulate allogeneic immune cell responses. Blood. 2005; 105:1815-22.
Al Iori et al., Biological Basis of Bone Formation, Remodeling, and Repair—Part 1: Biochemical Signaling Molecules. Tissue Eng.: Part B. 2008; 14(3):259-73.
Akle et al., Immunogenicity of human amniotic epithelial cells after transplantation into volunteers. Lancet. 1981; 2(8254):1003-5.
Allen et al., Periosteum: biology, regulation, and response to osteoporosis therapies. Bone. 2004; 35:1003-12.
Allori et al., Biological basis of bone formation, remodeling, and repair—part II: extracellular matrix. Tissue Eng Part B Rev. 2008; 14(3):275-83.
Asplin et al., Differential regulation of the fibroblast growth factor (FGF) family by alpha(2)-macroglobulin: evidence for selective modulation of FGF-2-induced angiogenesis. Blood. 2001; 97(11):3450-7.
Atanassov, W. et al., Use of amniotic membranes as biological dressings in contemporary treatment of burns. Ann Med Burn Club. 1994; VII(4).
Babalola et al., Aggregation of dispersed human cytotrophoblastic cells: Lessons relevant to the morphogenesis of the placenta. Dev Biol. 1990; 137(1):100-8.
Bagot et al., Reconstructed human epidermis: absence of Langerhans cells and failure to stimulate allogeneic lymphocytes in vitro. Clin Exp Immunol. 1988; 71(1):138-43.
Bailo et al., Engraftment potential of human amnion and chorion cells derived from term placenta. Transplantation. 2004; 78(10):1439-48.
Baker et al., Metalloproteinase inhibitors: biological actions and therapeutic opportunities. J Cell Sci. 2002; 115(Pt 19):3719-27.
Bannasch et al., Treatment of chronic wounds with cultured autologous keratinocytes as suspension in fibrin glue. Zentralbl Chir. 2000; 125 Suppl 1:79-81 (Abstract).
Bergeson et al., Fetal membrane collagens: Identification of two new collagen alpha chains. Proc Natl Acad Sci USA. 1976; 73(8):2579-83.
Bertolami et al., The Role of Proteoglycans in Hard and Soft Tissue Repair. Grit Rev Oral Bioi Med. 1994; 5(3&4):311-37.
Bielby et al., The role of mesenchymal stem cells in maintenance and repair of bone. Int J Care Injured. 2007; 38S1:S26-32.
Borth et al., Alpha 2-macroglobulin, a multifunctional binding protein with targeting characteristics. FASEB J. 1992; 6(15):3345-53.
Branski, L.K. et al., Amnion in the treatment of pediatric partial-thickness facial burns. Burns. 2008; 34(3):393-9.
Bravo et al., Effect of Storage on Preservation Methods on Viability in Transplantable Human Skin Allografts. Burns. 2000; 26:367-78.
Bruder et al., Bone Regeneration by Implantation of Purified, Culture-Expanded Human Mesenchymal Stem Cells. J Ortho Res. 1998; 16:155-62.
Bruder et al., Mesenchymal Stem Cells in Osteobiology and Applied Bone Regeneration. Clin Ortho Rel Res. 1998; 355S:S247-56.
Bryant-Greenwood, G.D., The extracellular matrix of the human fetal membranes: structure and function. Placenta. 1998; 19(1):1-11.
Carter et al., Immunolocalization of collagen types I and III, tenascin, and fibronectin in intramembranous bone. J Histochem Cytochem. 1991; 39(5):599-606.
Chang et al., Rotator cuff repair with periosteum for enhancing tendon-bone healing: a biomechanical and histological study in rabbits. Knee Surg Sports Traumatol Arthrosc. 2009; 17(12):1447-53.
Chen et al., Enveloping of periosteum on the hamstring tendon graft in anterior cruciate ligament reconstruction. Arthroscopy. 2002; 18(5):27E.
Chen et al., Enveloping the tendon graft with periosteum to enhance tendon-bone healing in a bone tunnel: A biomechanical and histologic study in rabbits. Arthroscopy. 2003; 19(3):290-6.
Chen et al., Hypoxia and transforming growth factor-beta 1 act independently to increase extracellular matrix production by placental fibroblasts. J Clin Endocrinol Metab. 2005; 90(2):1083-90.
Chen, L. et al., Paracrine factors of mesenchymal stem cells recruit macrophages and endothelial lineage cells and enhance wound healing. PLoS One. 2008; 3(4):e1886.
Choi et al: "Full-Thickness Skin Wound Healing Using Human Placenta-Derived Extracellular Matrix Containing Bioactive Molecules", Tissue Engineering Part A, (2013); 19(3&4):329-339.
Clarke, Normal Bone Anatomy and Physiology. Clin J Am Soc Nephrol. 2008; 3:S131-9.
Davis, J.W., Skin transplantation with a review of 550 cases at the Johns Hopkins Hospital. Johns Hopkins Med J. 1910; 15.
De Rotth, Plastic repair of conjunctival defects with fetal membranes. Arch Ophthalmol. 1940; 23:522-5.
Devescovi et al., Growth factors in bone repair. Chir Organi Mov. 2007; 92:161-8.
Dickinson et al., Monoclonal anti-TNF-alpha suppresses graft vs host disease reactions in an in vitro human skin model. Cytokine. 1994; 6(2):141-6.
Dimitriadis, E., Cytokines, Chemokines and Growth Factors in Endometrium Related to Implantation. Human Repro Update. 2005; 11(6): 613-30.
Dioguardi, D. et al., Skin Substitutes in burn treatment—our experience. Ann Med Burn Club. 1990; 3(4).
Dwek, The periosteum: what is it, where is it, and what mimics it in its absence? Skeletal Radial. 2010; 39:319-23.
Fan et al., Synovium-Derived Mesenchymal Stem Cells: A New Cell Source for Musculoskeletal Regeneration. Tissue Eng: Part B. 2009; 15(1):75-86.
Fortunato et al., I. Organ Culture of Amniochorionic Membrane In Vitro. Am J Reprod Immunol. 1994; 32:184-7.
Fortunato et al., Inflammatory cytokine (interleukins 1, 6 and 8 and tumor necrosis factor-alpha) release from cultured human fetal membranes in response to endotoxic lipopolysaccharide mirrors amniotic fluid concentrations. Am J Obstet Gynecol. 1996; 174(6):1855-61.
Gajiwala, K. and Gajiwala, A.L., Evaluation of lyophilised, gamma-irradiated amnion as a biological dressing. Cell Tissue Bank. 2004; 5(2):73-80.
Gajiwala, K. and Gajiwala, A.L., Use of banked tissue in plastic surgery. Cell Tissue Bank. 2003; 4(2-4):141-6.
Galiano et al., Interaction between the insulin-like growth factor family and the integrin receptor family in tissue repair processes. Evidence in a rabbit ear dermal ulcer model. J Clin Invest. 1996; 98(11):2462-8.
Ganatra, M.A. and Durrani, K.M., Method of obtaining and preparation of fresh human amniotic membrane for clinical use. J Pak Med Assoc. 1996; 46(6):126-8.
Goldman, Growth factors and chronic wound healing: past, present, and future. Adv. Skin Wound Care. 2004; 17:24-35.
Grafix® Cellular Repair Matrix for the Treatment of Burns. Osiris Therapeutics, Inc. 2012.
Greenhalgh et al., PDGF and FGF stimulate wound healing in the genetically diabetic mouse. Am J Pathol. 1990; 136(6):1235-46.
Haberal, M. et al., The use of silver nitrate-incorporated amniotic membrane as a temporary dressing. Burns Incl Therm Inj. 1987; 13(2):159-63.
Hadjiiski, 0. and Anatassov, N., Amniotic membranes for temporary burn coverage. Ann Burns Fire Disasters. 1996; IX(2).
Hieber, A.D. et al., Detection of elastin in the human fetal membranes: proposed molecular basis for elasticity. Placenta. 1997; 18(4):301-12.
Hocking, A.M. and Gibran, N.S., Mesenchymal stem cells: paracrine signaling and differentiation during cutaneous wound repair. Exp Cell Res. 316(14):2213-9.
Hong et al., The effect of various concentrations of human recombinant epidermal growth factor on split-thickness skin wounds. Int Wound J. 2006; 3:123-30.
Huang et al., Human transforming growth factor beta.alpha 2-macroglobulin complex is a latent form of transforming growth factor beta. J Bioi Chem. 1988; 263(3):1535-41.

(56) References Cited

OTHER PUBLICATIONS

Hutmacher et al., Periosteal Cells in Bone Tissue Engineering. Tissue Eng. 2003; 9(Supp 1):S45-64.
Ilancheran et al., Human fetal membranes: a source of stem cells for tissue regeneration and repair? Placenta. 2009; 30:2-10.
Izumi et al., Mortality of first-time amputees in diabetics: a 10-year observation. Diabetes Res Clin Pracl. 2009; 83:126-31.
Jordan et al., Optimal analysis of composite cytokine responses during alloreactivity. J Immunol Methods. 2002; 260:1-14.
Kasi, N. et al., Human amniotic membrane as a versatile biological dressing—a preliminary report. J Pak Med Assoc. 1987; 37(11):290-2.
Kawai et al., Effects of adiponectin on growth and differentiation of human keratinocytes-implication of impaired wound healing in diabetes. Biochem Biophys Re. Commun. 2008; 374:269-73.
Keene et al., Human bone contains type III collagen, type VI collagen, and fibrillin: type III collagen is present on specific fibers that may mediate attachment of tendons, ligaments, and periosteum to calcified bone cortex. J Histochem Cytochem. 2011; 39:59-69.
Kesting et al., The role of allogenic amniotic membrane in burn treatment. J Burn Care Res. 2008; 29:907-16.
Kesting, M.R. et al., The role of allogenic amniotic membrane in burn treatment. J Burn Care Res. 2008; 29(6):907-16.
Ketheesan et al., The effect of cryopreservation on the immunogenicity of allogeneic cardiac valves. Cryobiology. 1996; 33:41-53.
Kim et al., Coexpression of myofibroblast and macrophage markers: novel evidence for an in vivo plasticity of chorioamniotic mesodermal cells of the human placenta. Lab Invest. 2008; 88:365-74.
Komarcevic et al., New views on the physiology of wound healing. Med Pregl. 2000; 53(9-10):479-83 (Abstract).
Komatsu et al., The Control of Fracture Healing and Its Therapeutic Targeting: Improving Upon Nature. J Cell Biochem. 2010; 109:302-11.
Koob, T.J. et al: "Biological properties of dehydrated human amnion/chorion composite graft: implications for chronic wound healing". International Wound Journal. (2013); 10(5): 493-500.
Kruse, F. E. et al., Cryopreserved Human Amniotic Membrane for Ocular Surface Reconstruction. Graefe's Archive Clin Exper Ophthalmol.2000; 238(1):68-75.
Kubo et al., "Immunogenicity of human amniotic membrane in experimental xenotransplantation" Invest Ophthalmol Vis Sci. Jun. 2001;42(7):1539-46.
Kubo et al., Immunogenicity of 1-3,7, Human Amniotic Membrane in Experimental 19, 15 Xenotransplantation, Invest Ophthalmol Visual Sci. 1991; 1539.
Kwan et al., Scar and contracture: biological principles. Hand Clin. 2009; 25:511-28.
Ley-Chavez, E. et al., Application of biological dressings from radiosterilized amnios with cobalt 60 and serologic studies on the handling of burns in pediatric patients. Ann Transplant. 2003; 8(4):469.
Lin, S.D. et al., Amnion overlay meshed skin autograft. Burns Incl Therm Inj. 1985; 11(5):374-8.
Liu et al., Increased matrix metalloproteinase-9 predicts poor wound healing in diabetic foot ulcers. Diabetes Care. 2009; 32:117-9.
Livingston et al., Mesenchymal stem cells combined with biphasic calcium phosphate ceramics promote bone regeneration. J Mal Sci: Mal Med. 2003; 14:211-8.
Lomas et al., Application of a high-level peracetic acid disinfection protocol to re-process antibiotic disinfected skin allografts. Cell Tissue Bank. 2004; 5:23-36.
Lorusso, R. et al., The treatment of superficial burns with biological and synthetic material: frozen amnion and biobrane. Ann Med Burn Club. 1989; 2(2).
Lue et al., Engagement of CD14 on human monocytes terminates T cell proliferation by delivering a negative signal to T cells. J Immunol. 1991; 147(4):1134-8.
Maddalena Soncini et al: "Isolation and characterization of mesenchymal cells from human fetal membranes", Journal of Tissue Engineering and Regenerative Medicine, (2007) 1:296-305.

Magatti et al., Human amnion mesenchyme harbors cells with allogeneic T-cell suppression and stimulation capabilities. Stem Cells. 2008; 26:182-92.
Magliacani, G., The surgical treatment of burns: skin substitutes. Ann Med Burn Club. 1990.
Majors et al., Characterization of human bone marrow stromal cells with respect to osteoblastic differentiation. J Orthop Res. 1997; 15:546-57.
Majors et al., Charcterization of Human Bone Marrow Stromal Cells with Respect to Osteoblastic Differentiation. J Ortho Res. 1997; 15:546-57.
Malak et al., Confocal immunofluorescence localization of collagen types I, III, IV, V and VI and their ultrastructural organization in term human fetal membranes. Placenta. 1993; 14(4):385-406.
Malhotra et al., Human amniotic membrane transplantation: Different modalities of its use in ophthalmology. World J. Transplant, Jun. 24, 2014; 4(2); 111-121.
Malizos et al., The healing potential of the periosteum Molecular aspects. Injury. 2005; 36S:S13-9.
Mathew, S. et al., Characterization of the interaction between a2macroglobulin and fibroblast growth factor-2: the role of hydrophobic interactions. Dept Pathol. pp. 123-129.
Meinert et al., Proteoglycans and hyaluronan in human fetal membranes. Am J Obstel Gynecol. 2001; 184(4):679-85.
Midura et al., Parathyroid Hormone Rapidly Stimulates hyaluronan Synthesis by Periosteal Osteoblasts in the Tibial Diaphysis of the Growing Rat. J Biol Chem. 2003; 278(51):51462-8.
Mwaura et al., The impact of differential expression of extracellular matrix metalloproteinase inducer, matrix metalloproteinase-2, tissue inhibitor of matrix metalloproteinase-2 and PDGF-AA on the chronicity of venous leg ulcers. Eur J Vasc Endovasc Surg. 2006; 31:306-10.
Nauth et al., Bone morphogenetic proteins in open fractures: past, present, and future. Injury. 2009; 40:S3 & S27-31.
Nedelec et al., The effect of interferon alpha 2b on the expression of cytoskeletal proteins in an in vitro model of wound contraction. J Lab Clin Med. 1995; 126:474-84.
Niknejad et al., Properties of the Amniotic Membrane for Potential Use in Tissue Engineering. Eur Cells Mat. 2008; 15:88-99.
Niknejad, H., et al., Properties of the Amniotic Membrane for Potential Use in Tissue Engineering European Cells and Materials (2008); 15:88-99.
O'Driscoll et al., The chondrogenic potential of periosteum decreases with age. J Ortho Res. 2001; 19:95-103.
Occleston et al., Prevention and reduction of scarring in the skin by Transforming Growth Factor beta 3 (TGFbeta3): from laboratory discovery to clinical pharmaceutical. J Biomater Sci Polym Ed. 2008; 19:1047-63.
Ohashi et al., Advanced glycation end products enhance monocyte activation during human mixed lymphocyte reaction. Clin Immunol. 2009; 134:345-53.
Onishi et al., Distinct and overlapping patterns of localization of bone morphogenetic protein (BMP) family members and a BMP type II receptor during fracture healing in rats. Bone. 1998; 22(6):605-12.
Ornella et al., Concise review: isolation and characterization of cells from human term placenta: outcome of the first international Workshop on Placenta Derived Stem Cells. Stem Cells. 2008; 26(2):300-11.
Page et al., Critiquing clinical research of new technologies for diabetic foot wound management. J Foot Ankle Surg. 2002; 41(4):251-9.
Paquet-Fifield et al., A role for pericytes as microenvironmental regulators of human skin tissue regeneration. J Clin Invest. 2009; 119:2795-806.
Paradowska et al., Constitutive and induced cytokine production by human placenta and amniotic membrane at term. Placenta. 1997; 18:441-6.
Parolini et al., Concise review: isolation and characterization of cells from human term placenta: outcome of the first international workshop on placenta derived stem cells. Stem Cells. 2008; 26(2):300-11.

(56) References Cited

OTHER PUBLICATIONS

Pascher et al., Biologies in the treatment of transplant rejection and ischemia/reperfusion injury. BioDrugs. 2005; 19(4):211-31.
Pastar et al., Role of keralinocytes in healing of chronic wounds. Surg Technol Int. 2008; 17:105-12.
Portmann-Lanz et al., Concise Review: Isolation and Characterization of Cells from Human Term Placenta: Outcome of the First International Workshop on Placenta Derived Stem Cells.
Portmann-Lanz et al., Isolation and characterization of mesenchymal cells from human fetal membranes. J Tissue Eng Regen Med. 2007; 1(4):296-305.
Portmann-Lanz et al., Placental mesenchymal stem cells as potential autologous graft for pre- and perinatal neuroregeneration. Am J Obslel Gynecol. 2006; 194:664-73.
Portmann-Lanz et al: "Placental mesenchymal stem cells as potential autologous graft for pre- and perinatal neuroregeneration". American Journal of Obstetrics & Gyneco Mosby. (2006); 194(3): 664-673.
Presta et al., Fibroblast growth factor/fibroblast growth factor receptor system in angiogenesis. Cytokine Growth Factor Rev. 2005; 16:159-78.
Ramakrishnan, K.M. and Jayaraman, V., Management of partialthickness burn wounds by amniotic membrane: a cost-effective treatment in developing countries. Burns. 1997; 23 Suppl1:833-6.
Rao, T.V. and Chandrasekharam, V., Use of dry human and bovine amnion as a biological dressing. Arch Surg. 1981; 116(7):891-6.
Ravishanker, R. et al., Amnion Bank—the use of long term glycerol preserved amniotic membranes in the management of superficial and superficial partial thickness burns. Burns. 2003; 29(4):369-74.
Reuss et al., Fibroblast growth factors and their receptors in the central nervous system. Cell Tissue Res. 2003; 313:139-57.
Saksela, et al., Presence of a2Macroglobulin in Normal but Not in Malignant Human Syncytiotrophoblasts. Cancer Res. 1981; 41,2507-13.
Sangwan et al., Treatment of uveitis: beyond steroids. Indian J Ophthalmol. 2009; 58(1):1-2.
Sawhney, C.P., Amniotic membrane as a biological dressing in the management of burns. Burns. 1989; 15(5):339-42.
Sekine et al., Role of passenger leukocytes in allograft rejection: effect of depletion of donor alveolar macrophages on the local production of TNF-alpha, T helper 1/T helper 2 cytokines, IgG subclasses, and pathology in a rat model of lung transplantation. J Immunol. 1997; 159:4084-93.
Sen et al., Oxygen, Oxidants, and Antioxidants in Wound Healing an Emerging Paradigm. Ann 1-79 NY Acad Sci.2002;957:239-49.
Shalaby et al., The involvement of human tumor necrosis factors-alpha and -bela in the mixed lymphocyte reaction. J Immunol. 1988; 141:499-503.
Shapiro, Bone development and tis relation to fracture repair. The role of mesenchymal osteoblasts and surface osteoblasts. Eur Cell Mat. 2008; 15:53-76.
Shen et al.. IL-6 and TNF-Synergistically Inhibit Allograft Acceptance. J Am Soc Nephrol. 2009; 20:1032-40.
Shimmura et al., Antiinflammatory effects of amniotic membrane transplantation in ocular surface disorders. Cornea. 2001; 20(4):408-13.
Singh, R. et al., Microbiological safety and clinical efficacy of radiation sterilized amniotic membranes for treatment of second-degree burns. Burns. 2007; 33(4):505-10.
Sonicini, M. et al., "Isolation and characterization of mesenchymal cells from human fetal membranes", *Journal of Tissue Engineering and Regenerative Medicine*, 1, pp. 296-305, Jun. 13, 2007 (Jun. 13, 2007).
Splichal, I. and Trebichaysky, I., Cytokines and other important inftammatory mediators in gestation and bacterial intraamniotic infections. Folia Microbial (Praha). 2001; 46(4):345-51.
Subbota et al., Abstracts I Cryobiology. 2006; 53:415.

Suet al., Molecular profile of endothelial invasion of three-dimensional collagen matrices: insights into angiogenic sprout induction in wound healing. Am J Physiol Cell Physiol. 2008; 295:C1215-29.
Tadmori et al., Suppression of the allogeneic response by human IL-1 0: a critical role for suppression of a synergy between IL-2 and TNF-alpha. Cytokine. 1994; 6:462-71.
Taylor et al., Function of Lymphocytes and Macrophages after Cryopreservation by Procedures for Pancreatic Islets: Potential for Reducing Tissue Immunogenicity. Cryobiology. 1988; 25:1-17.
Thiex et al., Tissue-specific cytokine release from human extra-placental membranes stimulated by lipopolysaccharide in a two-compartment tissue culture system. Reprod Bioi Endocrinol. 2009; 7:117.
Thivolet et al., Long-term survival and immunological tolerance of human epidennal allografts produced in culture. Transplantation. 1986; 42:274-80.
Toungouz et al., Alloactivation induced during mixed-lymphocyte reaction provokes release of tumor necrosis factor alpha and interleukin 6 by macrophages and primes them to lipopolysaccharides. Hum Immunol. 1993; 38:221-5.
Tredget et al., Hypertrophic scars, keloids, and contractures. The cellular and molecular basis for therapy. Surg Clin North Am. 1997; 77:701-30.
Tredget, E.E. et al., Transforming growth factor-beta in thermally injured patients with hypertrophic scars: effects of interferon alpha-2b. Plast Reconstr Surg. 1998; 102(5):1317-28; discussion 1329-30.
Trengove et al., Analysis of the acute and chronic wound environments: the role of proteases and their inhibitors. Wound Repair Regen. 1999; 7:442-52.
Tseng et al., Amniotic Membrane Transplantation With or Without Limbal Allografts for Corneal Surface Reconstruction in Patients with Limbal Stem Cell Deficiency. Arch Ophthalmol. 1998; 116(4):431-41.
Ucakhan et al., Nonpreserved human amniotic membrane transplantation in acute and chronic chemical eye injuries. Cornea. 2002; 21:169-72.
Uchide et al. "Possible Role of Proinflammatory and Chemoattractive Cytokines Produced by Human Fetal Membrane Cells in the Pathology of Adverse Pregnancy Outcomes Associated with Influenza Virus Infection." Hindawi Publishing Corporation, Mediators of Inflammation, vol. 2012, pp. 1-32.
Uchino, Y., et al: "Amniotic membrane immobilized poly(vinyl alcohol) hybrid polymer as an artificial cornea scaffold that supports a stratified and differentiated corneal epithelium". Journal of Biomedical Materials Research. Part B: Applied Biomater., (2007); 81B(1): 201-206.
Ugar, N. and Haberal, M., Comparison of various dressing materials used for out-patient burn treatment at our centre. Ann Med Burn Club. 1994; 7.
Vaalamo et al., Differential expression of tissue inhibitors of metalloproteinases (TIMP-1, -2, -3, and -4) in normal and aberrant wound healing. Hum Pathol. 1999; 30:795-802.
Validation of Analytical Procedures: Text and Methodology 02 (R1) (1994).
Waddington et al., Differential roles for small leucine-rich proteoglycans in bone formation. Eur Cell Mat. 2003; 6:12-21.
Wang et al., Interleukin-10 Modulation of Alloreactivity and Graft-Versus-Host Reactions. Transplantation. 2002; 74:772-8.
Wenstrup et al., Type V Collagen Controls the Initiation of Collagen Fibril Assembly. J Bioi Chem. 2004; 279(51):53331-7.
Wingenfeld et al., Cryopreservation of Osteochondral Allografts: Dimethyl Sulfoxide Promotes Angiogenesis and Immune Tolerance in Mice. J Bone Joint Surg Am. 2002; 84-A:1420-9.
Yu et al., Bone morphogenetic protein 2 stimulates endochondral ossification by regulating periosteal cell fate during bone repair. Bone. 2010; 47(1):65-73.
Zaga et al., Secretions of Interleukin-1 band Tumor Necrosis Factor a by Whole Fetal Membranes Depend on Initial Interactions of Amnion or Choriodecidua with Lipopolysaccharides or Group B Streptococci. Bioi Reprod. 2004; 71:1296-302.

(56) References Cited

OTHER PUBLICATIONS

Zaga-Ciavellina et al., In vitro secretion profiles of interleukin (IL)-1 beta, IL-6, IL-8, IL-10, and TNF alpha after selective infection with *Escherichia coli* in human fetal membrane. Reprod Bioi Endocrinol. 2007; 5:46.
Zhang X et al: "Mesenchymal progenitor cells derived from chorionic villi of human placenta for cartilage tissue engineering", Biochemical and Biophysical Research Communications, (2006) 340(3):944-952.
Office Action in U.S. Appl. No. 13/030,507 dated Mar. 1, 2013.
Office Action in U.S. Appl. No. 13/030,507 dated Jan. 30, 2014.
Office Action in U.S. Appl. No. 13/030,539; dated Oct. 9, 2012.
Office Action in U.S. Appl. No. 13/030,539 dated Jun. 7, 2013.
Office Action in U.S. Appl. No. 13/030,562 dated Oct. 10, 2012.
Office Action in U.S. Appl. No. 13/030,562 dated Jul. 2, 2013.
Office Action in U.S. Appl. No. 13/030,580; dated Feb. 14, 2013.
Office Action in U.S. Appl. No. 13/030,580; dated May 17, 2013.
Office Action in U.S. Appl. No. 13/030,595; dated May 9, 2013.
International Search Report and Written Opinion in PCT/US11/25459, dated May 3, 2011.
Int'l Prelim. Report on Patentability in PCT/US2011/025459 dated Aug. 30, 2012.
International Search Report and Written Opinion in PCT/US11/25465, dated Apr. 14, 2011.
Int'l Prelim. Report on Patentability in PCT/US2011/025465 dated Aug. 30, 2012.
International Search Report and Written Opinion in PCT/US11/25469, dated Apr. 27, 2011.
Int'l Prelim. Report on Patentability in PCT/US2011/025469 dated Aug. 30, 2012.
International Search Report and Written Opinion in PCT/US11/25478, dated May 25, 2011.
Int'l Prelim. Report on Patentability in PCT/US2011/025478 dated Aug. 30, 2012.
International Search Report and Written Opinion in PCT/US11/25490, dated Apr. 13, 2011.
Int'l Prelim. Report on Patentability in PCT/US2011/025490 dated Aug. 30, 2012.
Int'l Search Report and Written Opinion in PCT/US2011/025493 dated May 4, 2011.
Int'l Prelim. Report on Patentability in PCT/US2011/025493 dated Aug. 30, 2012.
International Search Report and Written Opinion in PCT/US11/25498, dated May 4, 2011.
International Search Report and Written Opinion mailed by the International Searching Authority dated Sep. 29, 2014 for application PCT/US2014/037208, filed on May 7, 2014 (Applicant—Osiris Therapeutics, Inc. II Inventor—Samson Tom, et al.) (19 pages).
Extended European Search Report dated Apr. 1, 2014 for application EP 11745341, filed on Feb. 18, 2011 and published as EP 2536824 on Dec. 26, 2012 (Applicant—Osiris Therapeutics, Inc.) (6 pages).
Response to Extended European Search Report filed on Oct. 28, 2014 for application EP 11745341, filed on Feb. 18, 2011 and published as EP 2536824 on Dec. 26, 2012 (Applicant—Osiris Therapeutics, Inc.) (13 pages).
Extended European Search Report dated Apr. 1, 2014 for application EP 11745343, filed on Feb. 18, 2011 and published as EP 2536823 on Dec. 26, 2012 (Applicant—Osiris Therapeutics, Inc.) (6 pages).
Response to Extended European Search Report filed on Oct. 29, 2014 for application EP 11745343, filed on Feb. 18, 2011 and published as EP 2536823 on Dec. 26, 2012 (Applicant—Osiris Therapeutics, Inc.) (14 pages).
Extended European Search Report dated Apr. 24, 2014 for application EP 11745347, filed on Feb. 18, 2011 and published as EP 2536825 on Dec. 26, 2012 (Applicant—Osiris Therapeutics, Inc.) (12 pages).
Response to Extended European Search Report issued filed on Nov. 4, 2014 for application EP 11745347, filed on Feb. 18, 2011 and published as EP 2536825 on Dec. 26, 2012 (Applicant—Osiris Therapeutics, Inc.) (17 pages).
Extended European Search Report dated Apr. 24, 2014 for application EP 11745353, filed on Feb. 18, 2011 and published as EP 2536417 on Dec. 26, 2012 (Applicant—Osiris Therapeutics, Inc.) (10 pages).
Response to Extended European Search Report filed on Nov. 4, 2014 for application EP 11745353, filed on Feb. 18, 2011 and published as EP 2536417 on Dec. 26, 2012 (Applicant—Osiris Therapeutics, Inc.) (13 pages).
Extended European Search Report dated Apr. 29, 2014 for application EP 11745360, filed on Feb. 18, 2011 and published as EP 2536826 on Dec. 26, 2012 (Applicant—Osiris Therapeutics, Inc.) (10 pages).
Response to Extended European Search Report filed on Nov. 5, 2014 for application EP 11745360, filed on Feb. 18, 2011 and published as EP 2536826 on Dec. 26, 2012 (Applicant—Osiris Therapeutics, Inc.) (15 pages).
Extended European Search Report dated May 9, 2014 for application EP 11745361, filed on Feb. 18, 2011 and published as EP 2536827 on Dec. 26, 2012 (Applicant—Osiris Therapeutics, Inc.) (8 pages).
Response to Extended European Search Report filed on Dec. 3, 2014 for application EP 11745361, filed on Feb. 18, 2011 and published as EP 2536827 on Dec. 26, 2012 (Applicant—Osiris Therapeutics, Inc.) (14 pages).
Restriction Requirement dated Feb. 11, 2016 for U.S. Appl. No. 14/056,101, filed Oct. 17, 2013 (Applicant—Osris therapeutics, Inc. // Inventor—Tom, et al.) (11 pages).
Non Final Rejection dated May 19, 2016 by the U.S. Patent and Trademark Office for U.S. Appl. No. 14/172,940, filed Feb. 5, 2014 and published US-2014-0294777-A1 on Oct. 2, 2014 (Inventor—Samson Tom et al; Applicant—Osiris Therapeutics, Inc.) (20 pages).
Non Final Rejection dated May 19, 2016 by the U.S. Patent and Trademark Office for U.S. Appl. No. 14/070,035, filed Nov. 1, 2013 and published US 2014-0127317 A1 on May 8, 2014 (Inventor—Timothy Jansen et al; Applicant—Osiris Therapeutics, Inc.) (12 pages).
Non Final Rejection dated Jun. 27, 2016 by the U.S. Patent and Trademark Office for U.S. Appl. No. 14/069,894, filed Nov. 1, 2013 and published US 2014-0140966 A1 on May 22, 2014 (Inventor—Samson Tom et al; Applicant—Osiris Therapeutics, Inc.) (13 pages).
Non Final Rejection dated Jun. 30, 2016 by the U.S. Patent and Trademark Office for U.S. Appl. No. 14/056,101, filed Oct. 17, 2013 and published US 2014-0037598 A1 on Feb. 6, 2014 (Inventor—Timothy Jansen et al; Applicant—Osiris Therapeutics, Inc.) (13 pages).
Non-Final Office Action dated Aug. 25, 2016 for U.S. Appl. No. 14/291,256, filed May 30, 2014 and published US 2014-0301986 A1 on Oct. 9, 2014 (Inventor—Tom, et al; Applicant—Osiris Therapeutics, Inc.) (19 pages).
Requirement for Restriction or Election dated Aug. 8, 2016 by the U.S. Patent and Trademark Office for U.S. Appl. No. 14/272,343, filed May 7, 2014 and published US-2015-0010609-A1 on Jan. 8, 2015 (Inventor—Tom, et al; Applicant—Osiris Therapeutics, Inc.) (9 pages).
Requirement for Restriction or Election dated Aug. 9, 2016 by the U.S. Patent and Trademark Office for U.S. Appl. No. 14/272,345, filed May 7, 2014 and published US 2015-0010610 A1 on Jan. 8, 2015 (Inventor—Tom, et al; Applicant—Osiris Therapeutics, Inc.) (10 pages).
Requirement for Restriction or Election dated Aug. 24, 2016 by the U.S. Patent and Trademark Office for U.S. Appl. No. 14/272,33, filed May 7, 2014 and published US 2015-0010506 A1 on Jan. 8, 2015 (Inventor—Jansen, et al; Applicant—Osiris Therapeutics, Inc.) (10 pages).
Examination Report dated Aug. 30, 2016 by the Canadian Intellectual Property Office for appication CA 279036, filed on Feb. 18, 2011 (Inventor—Jansen, et al; Applicant—Osiris Therapeutics, Inc.) (5 pages).

(56) References Cited

OTHER PUBLICATIONS

International Search Report mailed by the International Searching Authority dated Sep. 29, 2014 for application PCT/US2014/037204, filed on May 7, 2014 (Applicant—Osiris Therapeutics, Inc. // Inventor—Samson, Tom, et al.) (2 pages).
Written Opinion mailed by the International Searching Authority dated Sep. 29, 2014 for application PCT/US2014/037204, filed on May 7, 2014 (Applicant—Osiris Therapeutics, Inc. // Inventor—Samson, Tom, et al.) (15 pages).
International Preliminary Report on Patentability mailed by the International Searching Authority dated Nov. 8, 2016 for application PCT/US2014/037204, filed on May 7, 2014 (Applicant—Osiris Therapeutics, Inc. // Inventor—Samson, Tom, et al.) (18 pages).
International Preliminary Report on Patentability mailed by the International Searching Authority dated Nov. 8, 2016 for application PCT/US2014/037208, filed on May 7, 2014 (Applicant—Osiris Therapeutics, Inc. // Inventor—Samson, Tom, et al.) (17 pages).
Non-Final Office Action dated Dec. 15, 2016 by the U.S. Patent and Trademark Office for U.S. Appl. No. 14/272,345, filed May 7, 2014 and published US 2015-0010610 A1 on Jan. 8, 2015 (Inventor—Tom, et al; Applicant—Osiris Therapeutics, Inc.) (pp. 1-16).
International Search Report mailed by the International Searching Authority dated Sep. 29, 2014 for application PCT/US2014/037201, filed on May 7, 2014 (Applicant—Osiris Therapeutics, Inc. // Inventor—Samson, Tom, et al.) (3 pages).
Written Opinion mailed by the International Searching Authority dated Sep. 29, 2014 for application PCT/US2014/037201, filed on May 7, 2014 (Applicant—Osiris Therapeutics, Inc. // Inventor—Samson, Tom, et al.) (15 pages).
International Preliminary Report on Patentability mailed by the International Searching Authority dated Nov. 8, 2016 for application PCT/US2014/037201, filed on May 7, 2014 (Applicant—Osiris Therapeutics, Inc. // Inventor—Samson, Tom, et al.) (18 pages).
Non-Final Office Action dated Dec. 19, 2016 by the U.S. Patent and Trademark Office for U.S. Appl. No. 14/272,339, filed May 7, 2014 and published US 2015-0010506 A1 on Jan. 8, 2015 (Inventor—Jansen, et al; Applicant—Osiris Therapeutics, Inc.) (13 pages).
Communication pursuant to Article 94(3) EPC dated Nov. 4, 2016 by the European Patent Office for EP Application No. 11745360.5 on Feb. 18, 2011 and published as 2536826 on Dec. 26, 2012 (Applicant—Osiris Therapeutics, Inc.; Applicant—Timothy Jansen et al) (5 Pages).
Non Final Rejection dated Jan. 11, 2017 by the U.S. Patent and Trademark Office for U.S. Appl. No. 14/272,343, filed May 7, 2014 and published as US 2015-0010609 A1 on Jan. 8, 2015 (Applicant—Osiris Therapeutics, Inc.; Applicant—Samson Tom et al.) (17 Pages).
Communication pursuant to Rules 161(2) and 162 EPC dated Dec. 15, 2016 by the European Patent Office for EP Application No. 14891208.2 on May 7, 2014 (Applicant—Osiris Therapeutics, Inc.; Applicant—Timothy Jansen et al) (5 Pages).
Final Rejection dated Jan. 10, 2017 by the U.S. Patent and Trademark Office for U.S. Appl. No. 14/172,940, filed Feb. 5, 2014 and published as US 2014-0294777 A1 on Oct. 2, 2014 (Applicant—Osiris Therapeutics, Inc.; Applicant—Samson Tom et al.) (19 Pages).
Communication pursuant to Rules 161(2) and 162 EPC dated Dec. 16, 2016 by the European Patent Office for EP Application No. 14891336.1 on May 7, 2014 (Applicant—Osiris Therapeutics, Inc.; Applicant—Timothy Jansen et al) (2 Pages).
Communication pursuant to Rules 161(2) and 162 EPC dated Dec. 20, 2016 by the European Patent Office for EP Application No. 14891554.9 on May 7, 2014 and published as 3139936 on Mar. 15, 2017 (Applicant—Osiris Therapeutics, Inc.; Applicant—Timothy Jansen et al) (2 Pages).
Communication pursuant to Rules 161(2) and 162 EPC dated Dec. 15, 2016 by the European Patent Office for EP Application No. 14891208.2 on May 7, 2014 and published as 3139934 on Mar. 15, 2017 (Applicant—Osiris Therapeutics, Inc.; Applicant—Timothy Jansen et al) (2 Pages).

Office Action dated Jan. 24, 2017 by the Canadian Patent Office for CA Application No. 2,790,322, which was filed on Feb. 18, 2011 (Applicant—Osiris Therapeutics, Inc.; Applicant—Samson Tom et al.) (5 Pages).
Final Office Action dated Dec. 15, 2016 for U.S. Appl. No. 14/070,035, filed Nov. 1, 2013 and published as US 2014-0127317 A1 on May 8, 2014 (Applicant—Osris therapeutics, Inc. // Inventor Tom, et al.) (16 pages).
Communication pursuant to Rules 161(2) and 162 EPC dated Dec. 16, 2016 by the European Patent Office for EP Application No. 14891336.1 on May 7, 2014 and published as 3139935 on Mar. 15, 2017 (Applicant—Osiris Therapeutics, Inc.; Applicant—Timothy Jansen et al) (2Pages).
Office Action dated Jan. 25, 2017 by the International Searching Authority for International Application No. 2,790,325, which was filed on Feb. 18, 2011 (Applicant—Osiris Therapeutics, Inc.) (6 pages).
Office Action dated Jan. 24, 2017 by the Canadian Intellectual Property Office for Canadian Patent Application No. 2,790,436, filed Feb. 18, 2011 (Inventor—Tom et al.; Applicant—Osiris Therapeutics, Inc.) (6 pages).
Final Office Action dated May 9, 2017 by the U.S. Patent and Trademark Office for U.S. Appl. No. 14/291,256, filed May 30, 2014 and published as US 2014/0301986 on Oct. 9, 2014 (Inventor—Tom et al.; Applicant—Osiris Therapeutics, Inc.) (22 pages).
Final Office Action dated May 5, 2017 by the U.S. Patent and Trademark Office for U.S. Appl. No. 14/069,894, filed Nov. 1, 2013 and published as US 2014/0140966 on May 22, 2014 (Inventor—Tom et al.; Applicant—Osiris Therapeutics, Inc.) (18 pages).
Final Office Action dated Apr. 21, 2017 by the U.S. Patent and Trademark Office for U.S. Appl. No. 14/056,101, filed Oct. 17, 2013 and published as US 2014/0037598 on Feb. 6, 2014 (Inventor—Jansen et al.; Applicant—Osiris Therapeutics, Inc.) (13 pages).
Communication under Rule 71(3) EPC dated May 22, 2017 by the European Patent Office for European Patent Application No. 11745361.3, which was filed on Feb. 18, 2011 and published as 2536827 on Dec. 26, 2012 (Inventor—Tom et al.; Applicant—Osiris Therapeutics, Inc.) (66 pages).
Communication pursuant to Rules 161(2) and 162 EPC dated Dec. 15, 2016 by the European Patent Office for European Patent Application No. 14891208.2, which was filed on May 7, 2014 (Inventor—Jansen et al; Applicant—Osiris Therapeutics, Inc.) (2 Pages).
Non-Final Office Action dated Jan. 11, 2017 by the U.S. Patent and Trademark Office for U.S. Appl. No. 14/272,343, filed May 7, 2014 and published as US 2015/0010609 on Jan. 8, 2015 (Inventor—Tom et al.; Applicant—Osiris Therapeutics, Inc.) (17 pages).
Communication pursuant to Rules 161(2) and 162 EPC dated Dec. 20, 2016 by the European Patent Office for European Patent Application No. 14891554.9, which was filed on May 7, 2014 and published as 3139936 on Mar. 15, 2017 (Inventor—Jansen et al.; Applicant—Osiris Therapeutics, Inc.) (2 Pages).
Final Office Action dated Jan. 10, 2017 by the U.S. Patent and Trademark office for U.S. Appl. No. 14/172,940, filed Feb. 5, 2014 and published as US 2014/0294777 on Oct. 2, 2014 (Inventor—Tom et al.; Applicant—Osiris Therapeutics, Inc.) (19 pages).
Communication pursuant to Article 94(3) EPC dated Nov. 4, 2016 by the European Patent Office for European Patent Application No. 11745360.5 on Feb. 18, 2011 and published as 2536826 on Dec. 26, 2012 (Inventor—Jansen et al.; Applicant—Osiris Therapeutics, Inc.) (5 Pages).
Communication pursuant to Rules 161(2) and 162 EPC dated Dec. 16, 2016 by the European Patent Office for European Patent Application No. 14891336.1, which was filed on May 7, 2014 (Inventor—Jansen et al.; Applicant—Osiris Therapeutics, Inc.) (2 Pages).
Final Office Action dated Jul. 14, 2017 by the USPTO for U.S. Appl. No. 14/272,343, filed May 7, 2014 and published as US 2015/0010609 A1 on Jan. 8, 2015 (Applicant—Osiris Therapeutics, Inc.; Inventor—Samson Tom) (19 pages).
Final Office Action dated Jul. 14, 2017 by the USPTO for U.S. Appl. No. 14/272,345, filed May 7, 2014 and published as US 2015/

(56) References Cited

OTHER PUBLICATIONS

0010610 A1 on Jan. 8, 2015 (Applicant—Osiris Therapeutics, Inc.; Inventor—Samson Tom) (18 pages).
Final Office Action dated Jul. 21, 2017 by the USPTO for U.S. Appl. No. 14/272,339, filed May 7, 2014 and published as US 2015/0010506 A1 on Jan. 8, 2015 (Applicant—Osiris Therapeutics, Inc.; Inventor—Samson Tom) (16 pages).
Communication pursuant to Article 94(3) EPC dated Jul. 20, 2017 by the European Patent Office for EP Application No. 11745347.2, which was filed on Feb. 18, 2011 and published as EP 2536825 on Dec. 26, 2012 (Applicant—Osiris Therapeutics, Inc.) (5 pages).
Database WPI Week 200522, Thomson Scientific. London. GB; AN 2005-214449; XP-002774389 (2 pages).
Extended European Search Report and Written Opinion dated Oct. 17, 2017 by the European Patent Office for EP Patent Application No. 14891554.9, which was filed on May 7, 2014 and published as EP 3139936 on Mar. 15, 2017(Applicant—Osiris Therapeutics, Inc.) (13 pages).
Extended European Search Report and Written Opinion dated Oct. 13, 2017 by the European Patent Office for EP Patent Application No. 14891208.2, which was filed on May 7, 2014 and published as EP 3139934 on Mar. 15, 2017(Applicant—Osiris Therapeutics, Inc.) (7 pages).
Extended European Search Report and Written Opinion dated Oct. 13, 2017 by the European Patent Office for EP Patent Application No. 14891336.1, which was filed on May 7, 2014 and published as EP 3139935 on Mar. 15, 2017(Applicant—Osiris Therapeutics, Inc.) (7 pages).
Non Final dated Oct. 19, 2017 by the USPTO for U.S. Appl. No. 14/172,940, filed Feb. 5, 2014 and published as US 2014-0294777 A1 on Oct. 2, 2014(Applicant—Osiris Therapeutics, Inc.; Inventor—Samson Tom) (22 pages).
Office Action dated Oct. 23, 2017 by the Canadian Patent Office for CA Application No. 2,790,336, which was filed on Feb. 18, 2011 (Applicant—Osiris Therapeutics, Inc.) (5 pages).
Non-Final Office Action issued by the U.S. Patent & Trademark Office dated Mar. 10, 2015, for U.S. Appl. No. 14/070,040, filed Nov. 1, 2013 and published as US 2014-0127177 A1 on May 8, 2014 (Inventor—Tom, et al. // Applicant—Osiris Therapeutics, Inc.) (13 pages).
Final Office Action dated Nov. 30, 2015 for U.S. Appl. No. 14/070,040, filed Nov. 1, 2013 (Applicant—Osiris therapeutics, Inc. // Inventor—Tom, et al.) (11 pages).
Restriction Requirement dated Feb. 11, 2016 for U.S. Appl. No. 14/056,101, filed Oct. 17, 2013 (Applicant—Osiris therapeutics, Inc. // Inventor—Tom, et al.) (11 pages).
Non-Final Office Action dated Aug. 18, 2016 for U.S. Appl. No. 14/070,040, filed Nov. 1, 2013 and published as US 2014-0127177 A1 on May 8, 2014 (Inventor—Tom, et al; Applicant—Osiris Therapeutics, Inc.) (13 pages).
Final Rejection dated Feb. 17, 2017 by the U.S. Patent and Trademark Office for U.S. Appl. No. 14/070,040, filed Nov. 1, 2013 and published as US 2014-0127177 A1 on May 8, 2014 (Applicant—Osiris Therapeutics, Inc.) (12 pages).
Non-Final Office Action dated Jan. 10, 2018 by the USPTO for U.S. Appl. No. 14/070,035, filed Nov. 1, 2013 and published as US 2014/0127317 on May 8, 2014 (Applicant—Osiris Therapeutics, Inc.; Inventor—Timothy Jansen) (20 pages).
Notice of Allowance dated Jan. 10, 2018 by the USPTO for U.S. Appl. No. 14/070,040, filed Nov. 1, 2013 and published as US 2014/0127177 on May 8, 2014 (Applicant—Osiris Therapeutics, Inc.; Inventor—Samson Tom) (8 pages).
Office Action dated Oct. 30, 2017 by the Canadian Patent Office for CA Application No. 2,790,340, which was filed on Feb. 18, 2011 (Applicant—Osiris Therapeutics, Inc.) (4 Pages).
Intention to Grant dated Jan. 26, 2018 by the European Patent Office for Patent Application No. 11745341.5, which was filed on Feb. 18, 2011 and published as EP 2536824 on Dec. 26, 2012 (Inventor—Tom et al.; Applicant—Osiris Therapeutics, Inc.) (8 pages).

Non-Final Office Action dated Feb. 23, 2018 by the U.S. Patent and Trademark Office for U.S. Appl. No. 14/272,343, filed May 7, 2014 and published as US 2015/0010609 on Jan. 8, 2015 (Inventor—Tom et al.; Applicant—Osiris Therapeutics, Inc.) (13 pages).
Non-Final Office Action dated Feb. 23, 2018 by the U.S. Patent and Trademark Office for U.S. Appl. No. 14/291,256, filed May 30, 2014 and published as US 2014/0301986 on Oct. 9, 2014 (Inventor—Samson et al.; Applicant—Osiris Therapeutics, Inc.) (25 pages).
Non-Final Office Action dated Feb. 23, 2018 by the U.S. Patent and Trademark Office for U.S. Appl. No. 14/069,894, filed Nov. 1, 2013 and published as US 2014/0140966 on May 22, 2014 (Inventor—Tom et al.; Applicant—Osiris Therapeutics, Inc.) (16 pages).
Notice of Reasons for Rejection dated Feb. 6, 2018 by the Japanese Patent Office for Patent Application No. 2016-567041, which was filed on Nov. 7, 2016 (Inventor—Tom et al.; Applicant—Osiris Therapeutics, Inc.) (Original—2 pages // Translation—2 pages).
Office Action dated Dec. 15, 2017 by the Canadian Patent Office for Patent Application No. 2,790,333, which was filed on Aug. 17, 2012 (Inventor—Samson et al.; Applicant—Osiris Therapeutics, Inc.) (5 pages).
Notice of Reasons for Rejection dated Feb. 27, 2018 by the Japanese Patent Office for Patent Application No. 2016-566997, which was filed on Nov. 7, 2016 (Inventor—Tom et al.; Applicant—Osiris Therapeutics, Inc.) (Original—4 pages // Translation—4 pages).
Issue Notification dated Apr. 11, 2018 by the U.S. Patent and Trademark Office for U.S. Appl. No. 14/070,040, filed Nov. 1, 2013 and published as US 2014/0127177 on May 8, 2014 (Applicant—Osiris Therapeutics, Inc.; Inventor—Samson Tom) (1 page).
Non-Final Office Action dated Mar. 26, 2018 by the U.S. Patent and Trademark Office for U.S. Appl. No. 14/272,345, filed May 7, 2014 and published as US 2015/0010610 on Jan. 8, 2015 (Inventor—Tom et al.; Applicant—Osiris Therapeutics, Inc.) (18 pages).
Non-Final Office Action dated May 17, 2018 by the U.S. Patent and Trademark Office for U.S. Appl. No. 14/056,101, filed Oct. 17, 2013 and published as US 2014/0037598 on Feb. 6, 2014 (Inventor—Tom et al.; Applicant—Osiris Therapeutics, Inc.) (14 pages).
Office Action dated Apr. 5, 2018 by the Canadian Intellectual Property Office for Patent Application No. 2,790,436, which was filed on Aug. 17, 2012 (Inventor—Tom et al.; Applicant—Osiris Therapeutics, Inc.) (6 pages).
Extended European Search Report dated May 4, 2018 by the European Patent Office for Patent Application No. 17205385.2, which was filed on Dec. 5, 2017 (Inventor—Tom et al.; Applicant—Osiris Therapeutics, Inc.) (8 pages).
Extended European Search Report dated May 24, 2018 by the European Patent Office for Patent Application No. 17207766.1, which was filed on Dec. 15, 2017 (Inventor—Tom et al.; Applicant—Osiris Therapeutics, Inc.) (9 pages).
Office Action dated Apr. 5, 2018 by the Canadian Intellectual Property Office for Patent Application No. 2,790,325, which was filed on Aug. 17, 2012 (Inventor—Tom et al.; Applicant—Osiris Therapeutics, Inc.) (6 pages).
Extended European Search Report dated May 25, 2018 by the European Patent Office for Patent Application No. 17211018.1, which was filed on Dec. 29, 2017 (Inventor—Jansen et al.; Applicant—Osiris Therapeutics, Inc.) (11 pages).
Extended European Search Report dated Apr. 24, 2018 by the European Patent Office for Patent Application No. 17211013.2, which was filed on Dec. 29, 2017 (Inventor—Tom et al.; Applicant—Osiris Therapeutics, Inc.) (10 pages).
Office Action dated Apr. 30, 2019 by the Canadian Intellectual Property Office for CA Application No. 2,790,436, which was filed on Feb. 18, 2011 (Applicant—Osiris Therapeutics, Inc.) (6 pages).
Office Action dated Apr. 30, 2019 by the Canadian Intellectual Property Office for CA Application No. 2,790,325, which was filed on Feb. 18, 2011 (Applicant—Osiris Therapeutics, Inc.) (6 pages).
U.S. Appl. No. 61/338,464, filed Feb. 18, 2010, Jennifer Michelle Marconi (Osiris Therapeutics, Inc.).
U.S. Appl. No. 61/338,489, filed Feb. 18, 2010, Jennifer Michelle Marconi (Osiris Therapeutics, Inc.).
U.S. Appl. No. 61/369,562, filed Jul. 30, 2010, Timothy Jansen (Osiris Therapeutics, Inc.).

(56) References Cited

OTHER PUBLICATIONS

U.S. Appl. No. 13/030,507 (2011/0212158), filed Feb. 18, 2011 (Sep. 1, 2011), Samson Tom (Osiris Therapeutics, Inc.)
U.S. Appl. No. 14/272,343 (2015/0010609), filed May 7, 2014 (Jan. 8, 2015), Samson Tom (Osiris Therapeutics, Inc.).
U.S. Appl. No. 14/291,256 (2014/0301986), filed May 30, 2014 (Oct. 9, 2014), Samson Tom (Osiris Therapeutics, Inc.).
U.S. Appl. No. 13/030,539 (2011/0212063), filed Feb. 18, 2011 (Sep. 1, 2011), Samson Tom (Osiris Therapeutics, Inc.).
U.S. Appl. No. 14/069,894 (2014/0140966), filed Nov. 1, 2013 (May 22, 2014), Samson Tom (Osiris Therapeutics, Inc.).
U.S. Appl. No. 13/030,551 (2011/0256202), filed Feb. 18, 2011 (Oct. 20, 2011), Samson Tom (Osiris Therapeutics, Inc.).
U.S. Appl. No. 14/172,940 (2014/0294777), filed Feb. 5, 2014 (Oct. 2, 2014), Samson Tom (Osiris Therapeutics, Inc.).
U.S. Appl. No. 14/272,345 (2015/0010610), filed May 7, 2014 (Jan. 8, 2015), Samson Tom (Osiris Therapeutics, Inc.).
U.S. Appl. No. 13/030,562, filed Feb. 18, 2011, Samson Tom (Osiris Therapeutics, Inc.).
U.S. Appl. No. 14/070,035 (2014/0127317), filed Nov. 1, 2013 (May 8, 2014), Timothy Jansen (Osiris Therapeutics, Inc.).
U.S. Appl. No. 13/030,580 (2011/0212064), filed Feb. 18, 2011 (Sep. 1, 2011), Timothy Jansen (Osiris Therapeutics, Inc.).
U.S. Appl. No. 14/056,101 (2014/0037598), filed Oct. 17, 2013 (Feb. 6, 2014), Timothy Jansen (Osiris Therapeutics, Inc.).
U.S. Appl. No. 14/272,339 (2015/0010506), filed May 7, 2014 (Jan. 8, 2015), Timothy Jansen (Osiris Therapeutics, Inc.)
U.S. Appl. No. 13/030,595 (2011/0212065), filed Feb. 18, 2011 (Sep. 1, 2011), Samson Tom (Osiris Therapeutics, Inc.).
U.S. Appl. No. 14/070,040 (U.S. Pat. No. 9,956,248), filed Nov. 1, 2013 (May 1, 2018), Samson Tom (Osiris Therapeutics, Inc.).
Non Final Rejection dated Jun. 13, 2019 by the USPTO for U.S. Appl. No. 14/070,035, filed Nov. 1, 2013 and published as US 2014-0127317 A1 on May 8, 2014 (Inventor—Timothy Jansen)(9 pages).
Communication pursuant to Article 94(3) EPC dated Jul. 24, 2019 by the European Patent Office for EP Application No. 11745360.5, which was filed on Feb. 18, 2011 and published as EP 2536826 on Dec. 26, 2012 (Applicant—Osiris Therapeutics, Inc.)(3 pages).

\* cited by examiner

METHODS OF MANUFACTURE OF THERAPEUTIC PRODUCTS COMPRISING VITALIZED PLACENTAL DISPERSIONS

RELATED APPLICATIONS

This application is a continuation of U.S. patent application Ser. No. 14/070,040, filed Nov. 1, 2013, now issued U.S. Pat. No. 9,956,248, which is a continuation of U.S. patent application Ser. No. 13/030,595, entitled Methods of Manufacture of Therapeutic Products Comprising Vitalized Placental Dispersions, filed on Feb. 18, 2011, which claims priority to:

U.S. Provisional Application Ser. No. 61/338,464 entitled "Selectively Immunodepleted Chorionic Membranes", filed on Feb. 18, 2010, U.S. Provisional Application Ser. No. 61/338,489 entitled "Selectively Immunodepleted Amniotic Membranes", filed on Feb. 18, 2010, and U.S. Provisional Application Ser. No. 61/369,562 entitled "Therapeutic Products Comprising Vitalized Placental Dispersions filed on Jul. 30, 2010, the contents of which are hereby incorporated by reference in their entireties.

This application is being co-filed on Feb. 18, 2011 with, and incorporates by reference, applications entitled:

"Immunocompatible Chorionic Membrane Products",

"Methods of Manufacture of Immunocompatible Chorionic Membrane" Products,

"Immunocompatible Amniotic Membrane Products",

"Methods of Manufacture of Immunocompatible Amniotic Membrane Products", and

"Therapeutic Products Comprising Vitalized Placental Dispersions".

TECHNICAL FIELD

The present invention relates to placental products, methods of medical treatment using placental products, and methods of making placental products.

BACKGROUND

The structural integrity of tissue is achieved, in part, by a dynamic interaction of the tissue with bioactive molecules, extracellular matrix, and a host of circulating cell types. Such interactions are also pivotal during tissue aging, injury, restorative and regenerative treatments. For example, burns produce local tissue damage as well as systemic consequences. Currently, treatment of burn wounds is focused on promoting healing and decreasing the risk of infection. Burn wounds continue to be a frustrating and serious problem in the clinic, and these wounds are often accompanied by high morbidity and mortality rates. The standard of care for burns includes the use of antiseptics and gauze wound dressings. However, for severe and large surface area burns, this treatment is not satisfactory. The gold standard for severe burn treatment continues to be autologous living skin grafts. However, the amount of skin available for grafting is often extremely limited, and this procedure always results in donor site wounds.

Attempts to improve burn wound care have included the use of a single growth factor or cocktail of growth factors as well as biological skin substitutes. Growth factors such as epidermal growth factor (EGF), platelet derived growth factor (PDGF), basic fibroblast growth factor (FGF), vascular endothelial growth factor (VEGF), and other singular factors have been tested in burn wound healing; however, with varying results.

The use of placental membranes for burns and other types of wounds originated more than 100 years ago (reviewed by Kesting et al., 2008). Placental membranes contain components that are present in skin and required for wound healing such as extracellular matrix, growth factors, and cells, including MSCs that are responsible for orchestrating the process of wound healing. The effectiveness of placental membranes such as amniotic membranes for burns was recorded in a number of published reports; however, the use of placental membranes for large surface area burns is limited due to challenges in providing sufficient placental membranes to cover large areas.

What is needed in the art is a therapeutic product that provides the benefits of placental membranes yet can be applied in fluid form. Moreover, needed is a product that provides dynamic therapy throughout more than one, optimally all, of the phases of wound repair: inflammatory, proliferative, and remodeling.

SUMMARY OF THE INVENTION

The present invention provides methods of manufacturing placental products comprising placental cells and a placental dispersion comprising placental factors. The placental cells and the placental dispersion are derived from placental tissue, e.g. a whole placenta or portion thereof. Placental tissue can be obtained by mechanical manipulation (e.g. dissection) or enzymatic digestion or combinations thereof. A placental tissue can optionally be an amnion, chorion, a mixture of amnion and chorion, or other tissue described here.

The present invention also provides a method of treating a tissue injury (e.g. wound or burn) comprising administering to a patient in need thereof a placental product of the present invention.

Optionally, the placental dispersion is a homogenate.

Optionally, placental factors present include extracellular matrix components.

Optionally, the placental dispersion comprises one or more placental factors set forth in Table 1, Table 2, Table 3, or Table 5.

Optionally, the placental cells comprise stromal cells such as MSCs (mesenchymal stem cells) and PSCs (placental stem cells).

In one embodiment, the method of making a placental product is a parallel processing method that comprises:
i) obtaining a first placental (e.g. amniotic or chorionic) tissue;
ii) obtaining placental cells from the first placental tissue;
iii) obtaining a second placental (e.g. amniotic or chorionic) tissue;
iv) disrupting the second placental tissue to form a dispersion comprising placental factors;
v) combining the placental cells and the dispersion to form the placental product.

Optionally, the first placental tissue and the second placental tissue are autologous to each other, for example, derived from the same donor.

In one embodiment, the method of making a placental product is a serial processing method wherein the second placental tissue is derived from the first placental tissue after said step of isolating the placental cells from a first placental tissue. For example, a first chorionic tissue may be retained after isolating a population of cells thereof, and then disrupted to form a dispersion. The dispersion may then be combined with the placental cells.

Optionally, the step of isolating the placental cells comprises contacting the first placental tissue (e.g. amnion or a chorion or a chorion lacking trophoblasts) with a digestive enzyme, such as a collagenase II. Optionally, the first placental tissue is exposed to a limited digestion with an enzyme such as collagenase II; e.g. exposure for less than about 1 hour (e.g. about 10 minutes or about 20 minutes).

Optionally, the placental tissue (from which the placental dispersion is produced) is chorionic tissue depleted of trophoblasts by treatment with a digestive enzyme such as dispase II followed by physical removal.

In another embodiment, the method of making a placental product comprises:
i) obtaining a placental (e.g. amniotic or chorionic) tissue;
ii) exposing the placental tissue to collagenase;
iii) dividing the placental tissue into a first portion and a second portion;
iv) isolating placental cells from the first placental portion;
v) disrupting the second placental portion to form a dispersion comprising placental factors; and
vi) combining the placental cells and the placental dispersion to form the placental product.
vii) In another embodiment, the method of making a placental product comprises:
viii) obtaining a placental (e.g. amniotic or chorionic) tissue;
ix) exposing the placental tissue to a collagenase for a time sufficient to release placental cells;
x) isolating the released placental cells from the collagenase exposed placental tissue;
xi) disrupting the collagenase exposed placental tissue to form a dispersion comprising placental factors; and
xii) combining the placental cells and the placental dispersion to form the placental product.

DETAILED DESCRIPTION OF THE INVENTION

Figure 1:
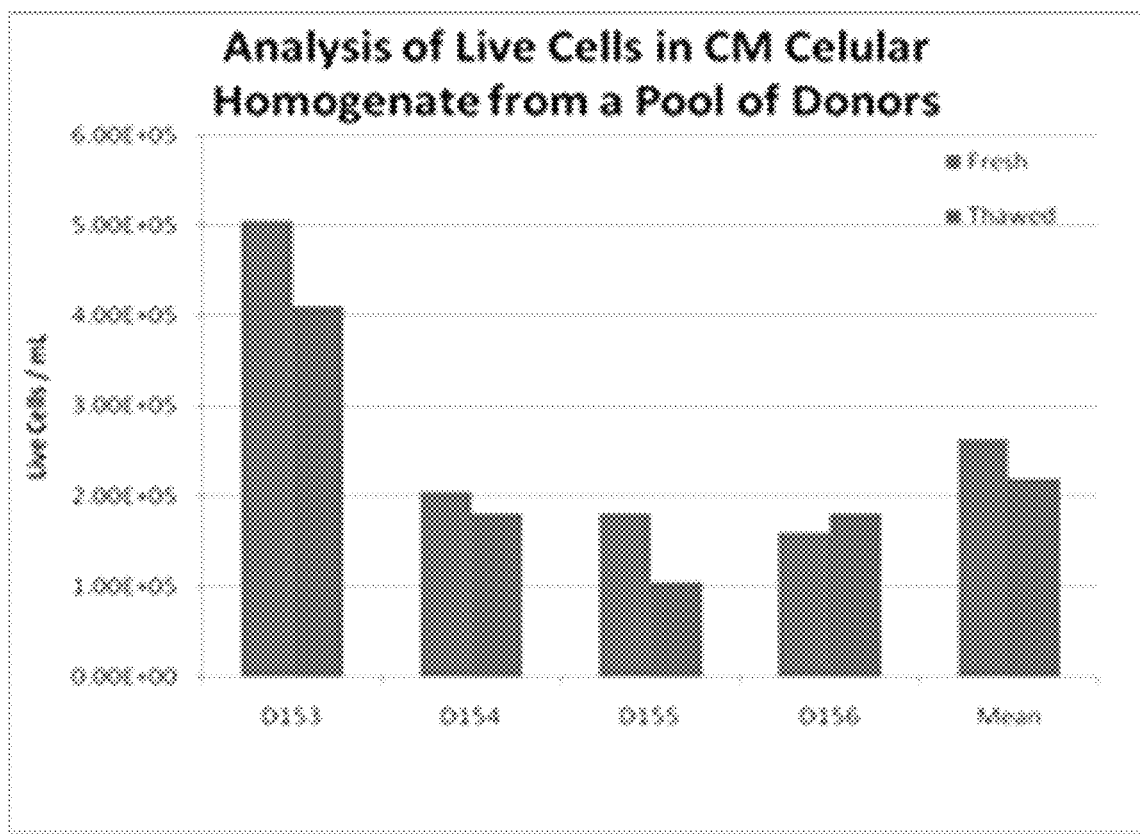
FIG. 1 depicts cell viability, before and after a freeze-thaw cycle of a placental product comprising isolated cells and a placental dispersion.

As used here, the following definitions and abbreviations apply.

"Chorionic tissue" or "Chorionic membrane" means the chorion or a portion thereof, e.g. the trophoblast, the somatic mesoderm, or combinations thereof.

"Examplary" (or "e.g." or "by example") means a non-limiting example.

"Placental dispersion" means a product formed by physical/mechanical disruption of placental tissue. For example, a dispersion may be in the form of a homogenate, a blend, a suspension, a colloid, or a solution.

"Placental tissue" means tissue derived from the placenta in the broadest sense of the word. Placental tissue can be a whole placenta or any portion thereof. "Portions of the placenta" is meant to include chorion, amnion, a chorion and amniotic membrane (e.g. amnio-chorion), Wharton's jelly, umbilical cord, placental cotyledons or combinations thereof. The placental tissue may be dissected or digested (or combinations thereof) to remove portions, membrane, or structures.

"Placental cells" means any cell that can be obtained from a placenta, without regard to genetic origin (e.g. maternal vs. fetal), developmental origin (e.g. endodermal, ectodermal, or mesodermal), or differentiation. Placental cells may comprise any placental cells known in the art, for example, mesenchymal stem cells (MSCs), endometrial stromal cells (ESCs), placenta-derived mesenchymal progenitor cells, placental mesenchymal stem cells, fibroblasts, epithelial cells, placental mesenchymal cells, macrophages, and the like.

"Placental cells" are further meant to require some feature of live cells such as one or more of metabolic activity, structural integrity (e.g. exclusion of a viability stain such as methylene blue), mitotic activity, signal transduction, and the like.

"Placental factor" means any product that is obtainable from a placental tissue (or placental cells). The product can be an angiogenic factor, chemokine, cytokine, growth factor, protease, protease inhibitor, or matrix component. Examplary placental factors are listed in Table 1, Table 2, Table 3, and Table 5.

"Tissue injury" means an injury of any tissue such as skin or the outer layer of any organ. By injury, it is meant a pathology that involves or results from an mechanical, metabolic or other insult. Examples of such tissue injuries are burns, wounds, ulcerations, and lacerations, ablations (including laser, freezing, cryo-surgery, heat and electrical ablations), and surgical incisions.

Placental Product

Overview

It has been surprisingly discovered that a placental product can now be produced by combining placental cells and a placental dispersion to produce a medicinal product of substantial and superior therapeutic value when administered to a tissue injury. The placental product has several advantageous properties.

Fluidity.

The placental product shares certain properties of a fluid such as an ability to deform under an applied stress and can be quantified measurements of viscosity. Thus, the present placental product can be spread over the surface of the surface to which it is applied. For example, one ml of placental product can be spread topically to cover more than about any of about 1 cm$^2$, about 10 cm$^2$, about 25 cm$^2$, about 50 cm$^2$, or about 100 cm$^2$ of skin. This fluid property solves the problem of limited applicability of products that retain the non-elastic properties of tissue (e.g. skin grafts). Moreover, the fluidity of the present placental product now makes it practical for new uses such as application to articulating joints and curved surfaces. It also provides a means of rapid application.

Extended Release.

Extended release formulations, especially for topical pharmaceutical products, are especially problematic. Moreover, due to natural instabilities as well as metabolic degradation, topical formulations often exhibit substantial loss of activity with time after administration. Without being bound by theory, the inventors believe that the placental cells of the present placental products produce placental components after administration. Thus, the present placental products can contain placental components derived from the placental dispersion and derived from the placental cells and depletion of placental components can be reduced. Additionally, placental cells in the present placental product can produce placental factors (e.g. protease inhibitors) that reduce the metabolic degradation of placental factors.

Dynamic Responsivity.

Without being bound by theory, the inventors believe that presence of live placental cells provide to the placental product the capacity to respond to physiologic stimuli in a manner somewhat analogous to endogenous cells in situ. Evidence of dynamic responsivity includes stimulated release of placental factors or changes in the placental factor profile with time after administration.

Placental Cells

Placental cells may be obtained from any placental tissue (e.g. chorion). Placental cells may be obtained by processing placental tissue in any manner which retains cell viability of at least one cell type (e.g. MSCs). For example, placental cells may be isolated or purified from placental tissue (e.g. by collagenase digestion of the chorion) or may be obtained without isolation from one or more placental factors (e.g. extracellular matrix) or from other placental cells.

Placental cells may be obtained by any method known in the art. Useful methods of obtaining placental cells (e.g. chorionic cells) are described, for example, by Portmann-Lanz et al. ("Placental mesenchymal stem cells as potential autologous graft for pre- and perinatal neuroregeneration"; American Journal of Obstetrics and Gynecology (2006) 194, 664-73), ("Isolation and characterization of mesenchymal cells from human fetal membranes"; Journal Of Tissue Engineering And Regenerative Medicine 2007; 1: 296-305.), and (Concise Review: Isolation and Characterization of Cells from Human Term Placenta: Outcome of the First International Workshop on Placenta Derived Stem Cells").

In one embodiment, placental cells are obtained by contacting placental tissue with one or more digestive enzymes, for example, by immersing placental tissue (e.g. a chorion, or placental tissue lacking trophoblasts) in a solution containing the digestive enzyme. The digestive enzyme may be any digestive enzyme known in the art. The digestive enzyme may also be combination of enzymes. Examplary digestive enzymes include one or more: collagenases (e.g., collagenase I, II, III and IV), matrix metalloprotease, neutral proteases, papains, deoxyribonucleases, serine protease (e.g. trypsin, chymotrypsin, elastase), or any combination thereof.

In one embodiment, placental cells are obtained from a chorion by contacting a chorion (e.g. a chorion lacking trophoblasts) with a collagenase (e.g. collagenase II). The collagenase may present in any suitable concentration, for example, about 100 U/mL to about 1000 mL, and in any suitable collagenase solvent, such as DMEM, and at any suitable temperature, for example 37° C. The chorion may be contacted with the digestive enzyme for any suitable period of time. Optionally, the chorion is contacted with a collagenase (e.g. collagenase II) for less than about any of: about 3 hrs, about 2 hr, or about 1 hr. Optionally, the chorion is contacted with the collagenase (e.g. collagenase II) for less than about 1 hour, for example, less than about any of: about 60 min, about 50 min, about 40 min, about 30 min, about 20 min, about 15 min, about 10 min, or about 5 min. Optionally, the chorion is contacted with a collagenase for a limited period of time such that a substantial portion of the placental tissue is retained on a about 100 micron filter. Optionally, the chorion is contacted with collagenase II for a limited period of time such that a substantial portion of the placental tissue is retained on a 100 micron filter. Optionally, after the placental cells are obtained, the chorion is disrupted to form a dispersion and the population is combined with (e.g. added to) the dispersion.

Surprisingly, a step of obtaining placental cells before subjecting the placental tissue to tissue disruption results in substantially a greater number of cells generally and also results in a population of cells that more resemble the population in the placental tissue than population of cells that are obtained from disrupted placental tissue.

A placental product that comprises placental cells from placental tissue that has not been disrupted surprisingly provides a therapeutically effective amount of viable cells without the need for ex vivo expansion of the placental cells. Although ex vivo expansion is a known method of increasing the number of viable cells in a population, such a step often leads to changes in the population make-up or distribution of cell phenotype. For example, various cells in a population may expand at different rates and expansion may also induce differentiation. Accordingly, one embodiment of the present invention provides a placental product comprising placental cells derived from a placental tissue wherein the placental cells exhibits a phenotypic distribution of cells which is substantially similar to the cells of the placental tissue of origin.

Placental Dispersion

A placental dispersion may be provided by disrupting a placenta (e.g. a chorion). The disruption of placental tissue may be accomplished by any physical/mechanical method of disrupting tissue (i.e. use of a "tissue disruptor" or "means for disruption"). For example, disruption may comprise homogenization, maceration, use of a blender, crushing, or mincing. Disruption may additionally or alternatively comprise shearing, mincing, dicing, or chopping. Disruption may additionally or alternatively comprise sonication.

The placental tissue may be disrupted for any suitable duration which produces a dispersion from the placenta. For example, the placenta may be disrupted (e.g. homogenized) for less than about 20 sec, about 15 sec, about 10 sec, or about 5 seconds.

The placental tissue can be disrupted sufficient to form a placental product with fluid characteristic and yet retain viable cells. Accordingly, live cells in the placental products of the present invention can additionally comprise placental cells that are derived from the placental dispersion.

The extent of tissue disruption may be reduced by a prior enzymatic digestion step with a matrix degrading enzyme such a collagenase(s), a protease(s), or combinations thereof. Indeed, it has surprisingly been discovered that such prior digestion preserves viable cells in the placental dispersion. For example, the length of treatment by a tissue disruptor can be reduced by prior enzymatic digestion.

Placental Factors

A placental product of the present invention may comprise one or more placental factors where the placental factors are components of the placental dispersion or components released into the placental product by the placental cells or a combination thereof.

It has surprisingly been discovered that the content of placental factors in placental products made according to the present invention have an unexpected therapeutic value. Such content of placental factors as taught herein is accordingly referred to here as a "therapeutic profile".

In one embodiment of the present invention, a therapeutic profile is one that provides two or more, or three or more, or four or more placental factors listed in Table 1, Table 2, Table 3, or Table 5. Optionally, the placental factors are present in an amount of about 20% to about 500% of the mean concentration set forth in Table 1, Table 2, or Table 5. Optionally, the placental factors are present in an amount of about 20% to about 500% of the minimum and the maximum (respectively) of the values set forth in Table 1, Table 2, or Table 5

Placental factors, according to the present invention, can be placental-derived factors such as angiogenic factors, chemokines, cytokines, growth factors, matrix metalloproteases, extracellular matrix proteins (or "matrix proteins"), and combinations thereof. The present placental products can comprise any of these placental factors.

The present placental products can optionally comprise a therapeutic profile of one or more of a PDGF (e.g. PDGF-bb), EGF, FGF, TGF-β1, TGF-β3, and VEGF and/or one or more of IL-8, IL-6, and MCP-1.

Useful placental products of the present invention can have a therapeutic profile as set forth in Table 1, Table 2, Table 3, or Table 5.

Useful placental products of the present invention can have a therapeutic profile comprising at least 25% of the minimum concentration of one or more placental factors set forth in Table 1 and optionally no more than 400% of the maximum concentration of one or more placental factors set forth in Table 1. In one embodiment, the one or more placental factors comprise fibronectin, TIMP, TGFß1, bFGF, and MMPs (e.g. MMP1, 2, 4, 7, 8, 9, and 10).

Useful placental products of the present invention can have a therapeutic profile comprising four or more placental factors where at least two placental factors are extracellular matrix components (or fragment thereof).

Placental products of the present invention can comprise a therapeutic profile of one or more placental factors which promote the migration of epithelial cells into a wound area (e.g. HGF and/or KGF), optionally in combination with a growth factor such as TGF-δ1. Optionally the concentration of such placental factors is about 25% of the minimum values set forth in in Table 1 and optionally no more than 400% of the maximum concentration set forth in Table 1

Placental products can comprise a therapeutic profile of placental factors that are mitotic or growth promoting. Placental products can contain HGF and KGF. For example, HGF at a concentration of about 5,000 to about 200,000 pg/mL and KGF at a concentration of about 5,000 to about 400,000 pg/mL are present in an examplary placental product as detailed in Example 10. Optionally, such placental products are useful in preventing scaring or a useful therapy aid during re-epithelialization, Placental products of the present invention can comprise a therapeutic profile of placental factors comprising one or more angiogenic factors (e.g. VEGF and/or bFGF) and can optionally additionally comprise one or more growth factors (e.g. TGF-β1 and/or TGF-β2), Examplary placental products of the present invention contain a therapeutic profile of VEGF levels greater than about 10 pg/ml or greater than about 50 pg/ml or greater than about 100 pg/ml. For example, an examplary placental product can comprise greater than about 200 pg/ml as detailed in Example 10.

Examplary placental products of the present invention contain a therapeutic profile of bFGF levels greater than any of about 10 or 100 or 1,000 or 10,000 pg/ml. An examplary placental product can comprise greater than about 11,000 pg/mL, as detailed in Example 10. Optionally such FGF-comprising placental products are useful for burn wound healing.

Placental products of the present invention can comprise a therapeutic profile of TGF-β1 and TGF-β2. An examplary placental product, as detailed in Example 10, comprises bFGF, TGF-β1 and TGF-β2. Optionally, such placental products are useful when the skin pathology being treated involves an inflammatory or a scaring pathology.

Placental products of the present invention may comprise a therapeutic profile of one or more protease inhibitors, such as tissue inhibitors of matrix metalloproteinases (TIMPs), alpha-2 macroglobulin, and/or thrombospondins.

In one embodiment, a placental product (e.g. derived from chorion) comprises one or more protease inhibitors.

In one embodiment, a placental product (e.g. derived from chorion) comprises one or more protease inhibitors and extracellular matrix proteins In one embodiment, a placental product (e.g. derived from chorion) comprises one or more protease inhibitors and viable cells.

In one embodiment, a placental product (e.g. derived from chorion) comprises one or more protease inhibitors, extracellular matrix proteins, and viable cells.

Without being bound by theory, the present inventors believe that the surprising efficacy that characterizes placental products of the present invention result in an interaction between the placental cells and the placental factors comprising (1) growth factor(s), (2) protease inhibitor(s), and (3) extracellular matrix components. Growth factors can bind to extracellular matrix thereby protecting the growth factors from degradation and effectively extending the half life of the growth factors. Bioavailability can be further regulated by subsequent release or matrix degradation. Similarly, protease inhibitors in examplary placental products provide additional protection against protease degradation. The placental cells further can protect growth factors and other placental factors in the placental products from degradation by providing additional protease inhibitors and growth factors. Accordingly, such placental products can optionally maintain surprising product integrity for extended periods of time resulting in placental products that require less frequent applications and superior treatment of tissue injuries such as burns and wounds. Surprisingly, the growth factors in such placental products can demonstrate a longer half-life in comparison to other growth factor therapies such as ACCS.

Formulation

The placental products of the present invention are administered as a dermatologically acceptable pharmaceutical product. Optionally, active pharmaceutical ingredients or excipients or combinations thereof can be added.

Viscosity.

Viscosity values that are useful and desirable according to the present invention vary as a function of the indication being treated. For example, where broad coverage (i.e. large areas of skin) or lower concentrations of placental products are desired, a less viscous formulation is advantageous. Examples of less viscous formulations are those of about 1,000 cps to about 50,000 cps, or about 2,000 cps to about 25,000 cps, or about 2,000 cps to about 10,000 cps, or about 5,000 cps to about 15,000 cps. Such less viscous compositions facilitate spreading of applied composition.

Where more restricted coverage or higher levels of placental products are desired, a more viscous formulation is advantageous. Examples of more viscous formulations are about 20,000 cps to about 200,000 cps or about 50,000 cps to about 100,000 cps.

The skilled artisan will now readily recognize that the desired viscosity can be attained according to the present invention by adjustments of the dispersion method (discussed elsewhere herein) or by selection of a dermatologically acceptable thickening agent and empirically determining the concentration necessary to achieve the desired thickening agent.

The placental products of the present invention can optionally include one or more antibiotic, emollient, keratolytics agent, humectants, anti-oxidants, preservative, or combinations thereof.

In one embodiment, a placental product comprises albumin, such as HSA or BSA. Optionally, the placental product comprises an electrolyte solution, for example, to provide physiological osmolality and pH (e.g. Plasma-LyteA). Optionally, the placental product comprises a cryopreservative, such as DMSO, glycerol, sericin, sugars, or a mixture thereof.

In one embodiment, a placental product comprises albumin, an electrolyte solution, and a cryopreservative. Optionally, the therapeutic product comprises 1% to about 15% albumin by weight and about 5% to about 20% cryopreservative by volume (e.g. about 10%). Optionally, the albumin is HSA, the electrolyte solution is Plasma-Lyte A, and the cryopreservative is DMSO.

Manufacture

Overview

A placental product of the present invention may be manufactured from a placenta in any suitable manner that provides the technical features taught herein. Any placental tissue is useful according to the present invention. Each of the embodiments of the present invention set forth here are meant to specifically embrace placental products where the placental dispersion is a dispersion of chorion that is depleted of or lacking trophoblastic components.

According to the present invention, the placenta is processed to produce the placental dispersion and the placental cells.

In one embodiment, the placental dispersion and the placental cells are derived from a different placenta or different placental portion (e.g. parallel processing).

In one embodiment, the placental dispersion and the placental cells are derived from the same placenta or the same placental portion (e.g. sequential processing).

Manufacturing Method 1. In one embodiment, a placental product is manufactured by:
  obtaining a placental (e.g. chorionic) tissue;
  digesting the placental tissue with one or more matrix degrading enzymes (e.g. a collagenase, optionally collagenase II);
  obtaining placental cells from the digested placental tissue;
  disrupting the digested placental tissue with a tissue disruptor to form a placental dispersion comprising placental factors; and
  combining the placental cells and the placental dispersion to form the placental product.

Optional Manufacturing Method 2 In one embodiment, a placental product is manufactured by:
  obtaining a first placental (e.g. chorionic) tissue;
  digesting the first placental tissue with one or more matrix degrading enzymes (e.g. a collagenase, optionally collagenase II);
  obtaining placental cells from the digested first placental tissue;
  obtaining a second placental tissue;
  disrupting the second placental tissue with a tissue disruptor to form a placental dispersion comprising placental factors; and
  combining the placental cells and the placental dispersion to form the placental product.

For either Manufacture Method, the placental tissue can be a chorion tissue such as a chorion tissue that has been processed to reduce the number of trophoblastic cells.

Examplary placental products of the present invention can be manufactured or provided with a bandage or wound dressing.

Trophoblast Removal

In one embodiment, trophoblasts are depleted or removed to produce the placental tissue from which the placental cells or the placental dispersion or both are derived. Surprisingly, such a placental product has one or more of the following superior features:
  a. is substantially non-immunogenic;
  b. provides remarkable healing time; and
  c. provides enhanced therapeutic efficacy.

Trophoblasts may be removed in any suitable manner which substantially diminishes the trophoblast content of the placental product. Optionally, the trophoblasts are selectively removed or otherwise removed without eliminating a substantial portion of one or more therapeutic components from the placenta (e.g. MSCs, placental factors, etc). Optionally, the trophoblasts are removed before isolating a population of cells and/or disrupting the placental tissue.

One method of removing trophoblasts comprises treating the placenta (e.g. chorion or amino-chorion) with a digestive enzyme such as dispase (e.g. dispase II) and separating the trophoblasts from the placenta. Optionally, the step of separating comprises mechanical separation such as scraping. Optionally, scraping comprises scraping with a soft instrument such as a finger.

Useful methods of removing trophoblasts from a placenta (e.g. chorion) are described by Portmann-Lanz et al. ("Placental mesenchymal stem cells as potential autologous graft for pre- and perinatal neuroregeneration"; American Journal of Obstetrics and Gynecology (2006) 194, 664-73), ("Isolation and characterization of mesenchymal cells from human fetal membranes"; Journal Of Tissue Engineering And Regenerative Medicine 2007; 1: 296-305.), and (Concise Review: Isolation and Characterization of Cells from Human Term Placenta: Outcome of the First International Workshop on Placenta Derived Stem Cells").

Preservation

A placental product of the present invention may be used fresh or may be preserved for a period of time.

Also as depicted in FIG. 1, a placental product of the present invention, cell viability is retained surprisingly well after a freeze-thaw cycle In one embodiment, a placental product is cryopreserved. A placental product may be cryopreserved by freezing (e.g. a −80° C.). Freezing may comprise storage in a cryopreservation medium such as DMSO, glycerol, sericin, sugars, or mixtures thereof. Freezing may comprise, for example, incubating the placental product at 4° C. for 30-60 min, and then incubating at −80° C. until use. The placental product may then be thawed for use.

A placental product may be formulated in a cryopreservative before cryopreservation. Examplary cryopresevatives include DMSO, glycerol, and the like. The cryopreservative may further be formulated with additional components such as albumin (e.g. HSA or BSA), an electrolyte solution (e.g. Plasma-Lyte), or a combination thereof. Optionally, the placental product comprises 1% to about 15% albumin by weight and about 5% to about 20% cryopreservative by volume (e.g. about 10%).

Optionally, a placental product can be formed by the addition of cryopreserved placental cells of the present invention to a fresh (never frozen) placental dispersion or to a frozen placental dispersion or to a lyophilized placental dispersion.

Optionally, a placental product can be formed by the addition of fresh placental cells of the present invention to a frozen placental dispersion or to a lyophilized placental dispersion.

Methods of Use

The placental products of the present invention may be used to treat any tissue injury. A method of treatment may be provided, for example, by administering to a subject in need thereof, a placental product of the present invention.

A typical administration method of the present invention is topical administration. Administering the present invention can optionally involve administration to an internal tissue where access is gained by a surgical procedure.

Placental products can be administered autologously, allogeneically or xenogeneically.

In one embodiment, a present placental product is administered to a subject to treat a wound. Optionally, the wound is a laceration, scrape, thermal or chemical burn, incision, puncture, or wound caused by a projectile. Optionally, the wound is an epidermal wound, skin wound, chronic wound, acute wound, external wound, internal wounds, congenital wound, ulcer, or pressure ulcer. Such wounds may be accidental or deliberate, e.g., wounds caused during or as an adjunct to a surgical procedure. Optionally, the wound is closed surgically prior to administration.

In one embodiment, the injury is a burn. Optionally, the burn is a first-degree burn, second-degree burn (partial thickness burns), third degree burn (full thickness burns), infection of burn wound, infection of excised and unexcised burn wound, loss of epithelium from a previously grafted or healed burn, or burn wound impetigo.

In one embodiment, the injury is an ulcer, for example, a diabetic ulcer (e.g. foot ulcer).

In one embodiment, a placental product is administered by placing the placental product directly over the skin of the subject, e.g., on the stratum corneum, on the site of the wound, so that the wound is covered, for example, using an adhesive tape. Additionally or alternatively, the placental product may be administered as an implant, e.g., as a subcutaneous implant.

In one embodiment, a placental product is administered to the epidermis to reduce rhytids or other features of aging skin. Such treatment is also usefully combined with so-called cosmetic surgery (e.g. rhinoplasty, rhytidectomy, etc.).

In one embodiment, a placental product is administered to the epidermis to accelerate healing associated with a dermal ablation procedure or a dermal abrasion procedure (e.g. including laser ablation, thermal ablation, electric ablation, deep dermal ablation, sub-dermal ablation, fractional ablation, and microdermal abrasion).

Other pathologies that may be treated with placental products of the present invention include traumatic wounds (e.g. civilian and military wounds), surgical scars and wounds, spinal fusions, spinal cord injury, avascular necrosis, reconstructive surgeries, ablations, and ischemia.

In one embodiment, a placental product of the present invention is used in a tissue graft procedure. Optionally, the placental product is applied to a portion of the graft which is then attached to a biological substrate (e.g. to promote healing and/or attachment to the substrate). By way of non-limiting example, tissues such as skin, cartilage, ligament, tendon, periosteum, perichondrium, synovium, fascia, mesenter and sinew can be used as tissue graft.

In one embodiment, a placental product is used in a tendon or ligament surgery to promote healing of a tendon or ligament. Optionally, the placental product is applied to portion of a tendon or ligament which is attached to a bone. The surgery can be any tendon or ligament surgery, including, e.g. knee surgery, shoulder, leg surgery, arm surgery, elbow surgery, finger surgery, hand surgery, wrist surgery, toe surgery, foot surgery, ankle surgery, and the like. For example, the placental product can be applied to a tendon or ligament in a grafting or reconstruction procedure to promote fixation of the tendon or ligament to a bone.

Through the insight of the inventors, it has surprisingly been discovered that placental products of the present invention provide superior treatment (e.g. healing time and/or healing strength) for tendon and ligament surgeries. Tendon and ligament surgeries can involve the fixation of the tendon or ligament to bone. Without being bound by theory, the present inventors believe that osteogenic and/or chondrogenic potential of MSCs in the present placental products promotes healing process and healing strength of tendons or ligaments. The present inventors believe that the present placental products provide an alternative or adjunctive treatment to periosteum-based therapies. For example, useful periosteum based treatments are described in Chen et al. ("Enveloping the tendon graft with periosteum to enhance tendon-bone healing in a bone tunnel: A biomechanical and histologic study in rabbits"; Arthroscopy. 2003 March; 19(3):290-6), Chen et al. ("Enveloping of periosteum on the hamstring tendon graft in anterior cruciate ligament reconstruction"; Arthroscopy. 2002 May-June; 18(5):27E), Chang et al. ("Rotator cuff repair with periosteum for enhancing tendon-bone healing: a biomechanical and histological study in rabbits"; Knee Surgery, Sports Traumatology, Arthroscopy Volume 17, Number 12, 1447-1453), each of which are incorporated by reference.

As non-limiting example of a method of tendon or ligament surgery, a tendon is sutured to and/or wrapped or enveloped in a placental membrane and the tendon is attached to a bone. Optionally, the tendon is placed into a bone tunnel before attached to the bone.

In one embodiment, the tendon or ligament surgery is a graft procedure, wherein the placental product is applied to the graft. Optionally, the graft is an allograft, xenograft, or an autologous graft.

In one embodiment, the tendon or ligament surgery is repair of a torn ligament or tendon, wherein the placental product is applied to the torn ligament or tendon.

Non-limiting examples of tendons to which a placental product can be applied include a digitorum extensor tendon, a hamstring tendon, a bicep tendon, an Achilles Tendon, an extensor tendon, and a rotator cuff tendon.

In one embodiment, a placental product of the present invention is used to reduce fibrosis by applying the placental product to a wound site.

In one embodiment, a placental product of the present invention is used as an anti-adhesion wound barrier, wherein the placental product is applied to a wound site, for example, to reduce fibrosis (e.g. postoperative fibrosis).

Non-limiting examples of wound sites to which the placental product can be applied include those that are surgically induced or associated with surgery involving the spine, laminectomy, knee, shoulder, or child birth, trauma related wounds or injuries, cardiovascular procedures, angiogenesis stimulation, brain/neurological procedures, burn and wound care, and ophthalmic procedures. For example, optionally, the wound site is associated with surgery of the spine and the stromal side of the placental product is applied to the dura (e.g. the stromal side facing the dura). Direction for such procedures, including the selection of wound sites and/or methodologies, can be found, for example, in WO 2009/132186 and US 2010/0098743, which are hereby incorporated by reference.

A placental product of the present invention can optionally be used to reduce adhesion or fibrosis of a wound. Postoperative fibrosis is a natural consequence of all surgical wound healing. By example, postoperative peridural adhesion results in tethering, traction, and compression of the thecal sac and nerve roots, which cause a recurrence of hyperesthesia that typically manifests a few months after laminectomy surgery. Repeated surgery for removal of scar tissue is associated with poor outcome and increased risk of injury because of the difficulty of identifying neural structures that are surrounded by scar tissue. Therefore, experimental and clinical studies have primarily focused on preventing the adhesion of scar tissue to the dura matter and nerve roots. Spinal adhesions have been implicated as a major contributing factor in failure of spine surgery. Fibrotic scar tissue can cause compression and tethering of nerve roots, which can be associated with recurrent pain and physical impairment.

The placental products disclosed herein are useful in treating a number of wounds including: tendon repair, cartilage repair (e.g. femoral condyle, tibial plateau), ACL replacement at the tunnel/bone interface, dental tissue augmentation, fistulas (e.g. Crohn's disease, G-tube, tracheoesophogeal), missing tissue at adhesion barriers (e.g. nasal septum repair, vaginal wall repair, abdominal wall repair, tumor resection), dermal wounds (e.g. partial thickness burns, toxic epidermal necrolysis, epidermolysis bullosa, pyoderma gangrenosum, ulcers e.g. diabetic ulcers (e.g. foot), venous leg ulcers), surgical wounds, hernia repair, tendon repair, bladder repair, periosteum replacement, keloids, organ lacerations, epithelial defects, and repair or replacement of a tympanic membrane.

The presently described technology and its advantages will be better understood by reference to the following examples. These examples are provided to describe specific embodiments of the present technology. By providing these specific examples, it is not intended limit the scope and spirit of the present technology. It will be understood by those skilled in the art that the full scope of the presently described technology encompasses the subject matter defined by the claims appending this specification, and any alterations, modifications, or equivalents of those claims.

The citations provided herein are hereby incorporated by reference for the cited subject matter.

In the present specification, use of the singular includes the plural except where specifically indicated.

EXAMPLES

Example 1 Obtaining Placental Tissue

A whole placenta was obtained from a registered tissue bank after informed consent. The placenta and placed, with the maternal surface (rough surface) face down, on a sterile tray. The amniotic-chorionic membrane was cut and removed from the placenta. The chorionic membrane was then separated from the amnion and washed twice in PBS.

The chorionic membrane was then soaked in an anticoagulant (ACD-A) solution to remove blood clots and then washed again in PBS.

The chorionic membrane was then digested by incubation with dispase II for 30 min. at 37° C. The trophoblast layer was mechanically removed by scraping with fingers and the chorion was washed again in PBS.

The chorionic membrane was then incubated for 24 hours in an antibiotic cocktail containing gentamicin, vancomycin, and amphotericin B, and washed again in PBS.

Example 2 Digesting Placental Tissue

A chorion membrane (obtained from Example 1) was digested by incubation in 200 mL of a collagenase II solution (300 U/mL in DMEM) for 10 min at 37° C. The chorionic membrane was then removed, leaving a digestion suspension containing collagenase and placental cells.

The volume and container for digestion was determined based on the need to provide a suitable digestion environment for the tissue once placed on a shaker. The digestion was carried out on a standard plate shaker set at moderate speed in a 37° C. cell culture incubator.

Example 3 Obtaining Placental Cells

A digestion suspension comprising placental cells (obtained from Example 2) was centrifuged at 2000 rcf for 5 min to separate the digestive enzyme (collagenase II) from the placental cells. This step centrifugation step may enhance cell viability by preventing over-digestion and ensure that the enzyme is washed away before homogenizing the tissue. This centrifugation step pellets the cells without damaging them, allowing the collagenase II to be removed as supernatant.

The cells were then centrifuged again, the supernatant poured off, and the placental cells were resuspended in a small volume (2 mL) of cryprotectant (5% DMSO in saline). Two mL provides an adequate volume to resuspend the cells while not over-diluting the chorion membrane dispersion once the cells have been added.

Example 4 Obtaining a Placental Dispersion

A chorionic membrane (obtained from Example 2) was washed twice in PBS to remove residual digestion enzyme and placed in a homogenization container with 1 ml cryoprotectant per gram of chorionic membrane. This volume was determined to be appropriate for diluting the chorion membrane enough to produce a dispersion of ideal consistency while maintaining protein concentration at clinically significant levels.

The temperature of the chorionic membrane was reduced by placing the container on ice for greater than 10 min. The chorionic membrane was then homogenized twice at high speed for 5 sec. using a tissue homogenizer to obtain a chorionic dispersion (homogenate).

Once the chorion membrane is subjected to digestion, it becomes easy to homogenize. Surprisingly, only a small amount of homogenization is needed to create a homogenous solution ideal for clinical use and increases the amount of live cells present in the final dispersion.

Example 5 Providing a Placental Product

A placental dispersion (obtained from Example 4) was combined with viable isolated placental cells (obtained from Example 3) and mixed thoroughly to provide a placental product. The placental product may be used (e.g. for therapy) fresh or may first be preserved (e.g. cryogenically) for a period of time.

Example 6 Cryopreservation

A placental product (obtained from Example 5) was aliquoted into vials and incubated at 4° C. for 30-60 min. The vials were then frozen at −80° C. until use.

Example 7 Isolation of Cells without Complete Digestion of Placenta

Figure 2:
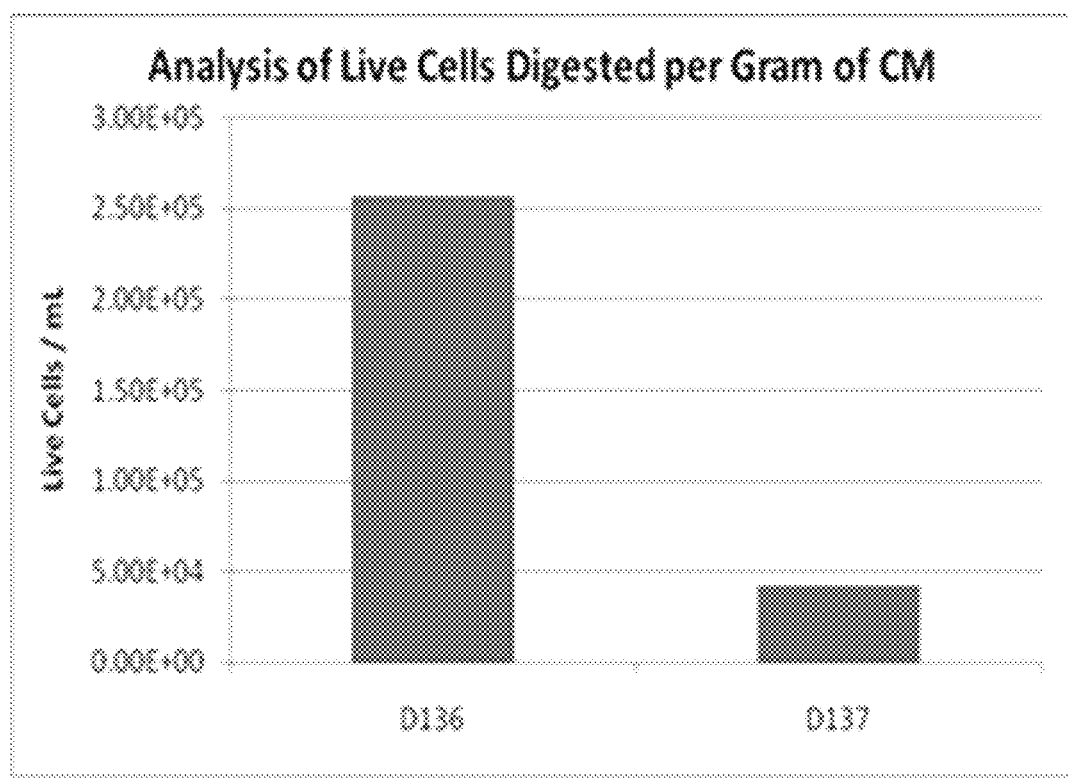
FIG. 2 depicts recovery of viable cells isolated by digestion.

The inventors tested whether a limited collagenase II digestion might be performed to obtain a suspension containing live cells and yet preserve the integrity of the placental tissue (e.g. preserve placental factors and remaining live cells). A brief 10 minute digestion with collagenase II left the tissue intact and made further handling possible. In addition, a 10 min. collagenase digestion was able to produce high numbers of viable cells Two placentas were obtained, each from a different donor, and processed according to the procedure detailed in Example 1 through Example 2, except a collagenase II concentration of 244 U/mL, as described above. A cell count was performed immediately following digestion to determine the number of viable cells per gram of tissue that each enzyme was able to digest away off the tissue. The data are presented in FIG. 2.

Figure 3:
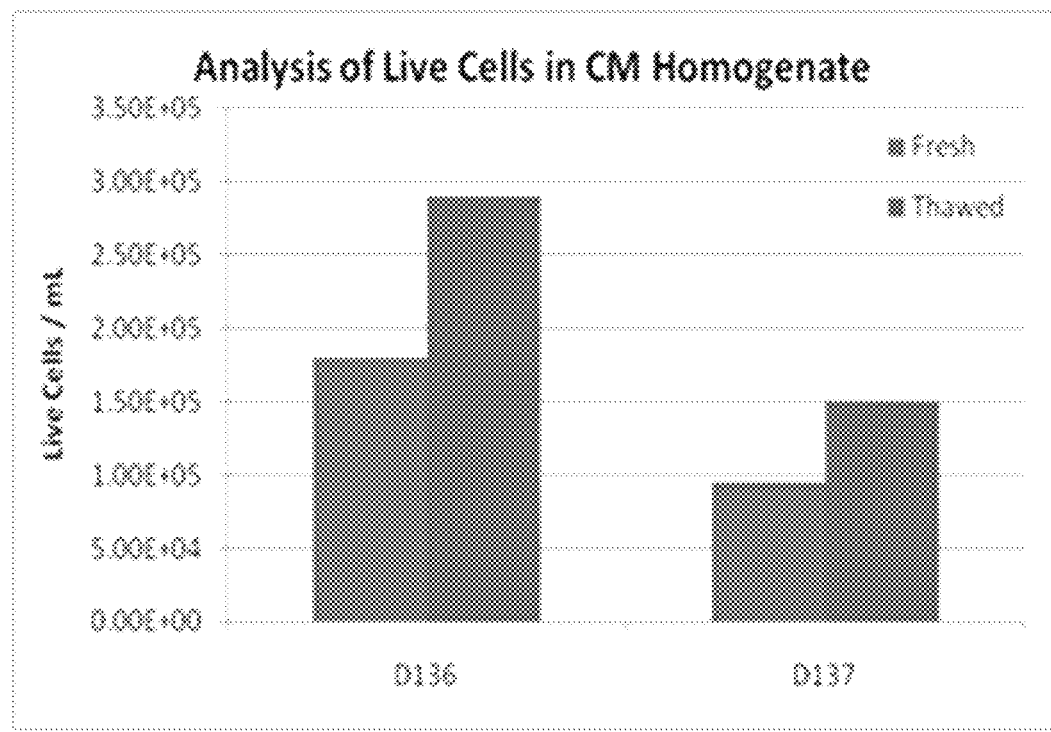
FIG. 3 depicts cell viability, before and after a freeze-thaw cycle of a placental product comprising isolated cells and a placental dispersion.

The placentas were further processed as described in Example 3 through Example 6. Before freezing and after thawing, cells were counted using a hemocytometer and trypan blue staining was used to distinguish live cells. The data are presented in FIG. 3.

Surprisingly, a substantial population of cells was isolated by digestion of less than 1 hr (e.g. 10 min). Digesting the tissue for only 10 min allowed the loosening and removal cells from the tissue without completely breaking up the tissue. In this manner, it was possible to separate the collagenase II/cell mixture from the chorionic membrane. The inventors discovered that 10 min was an adequate amount of digestion time and allowed for variances introduced as a result of donor variability. The digestion process allows isolation of as many live cells as possible while not disrupting the tissue integrity of the chorion membrane to a degree that makes it impossible to manipulate further. The chorion membrane could then be disrupted to produce a placental dispersion that was rich in placental factors while the cells could be isolated from the enzyme solution and then reintroduced to the dispersion to form the placental product.

Example 8 Isolation of Cells without Complete Digestion of Placental Tissue

Multiple placental products were prepared and cell counts were taken immediately following digestion (FIG. 4) and before freezing and after thawing (FIG. 1), using the procedure described in Example 7. Cells were counted using a hemocytometer and trypan blue staining was used to distinguish live cells. All cell count data was pooled and a mean was calculated.

Figure 4:
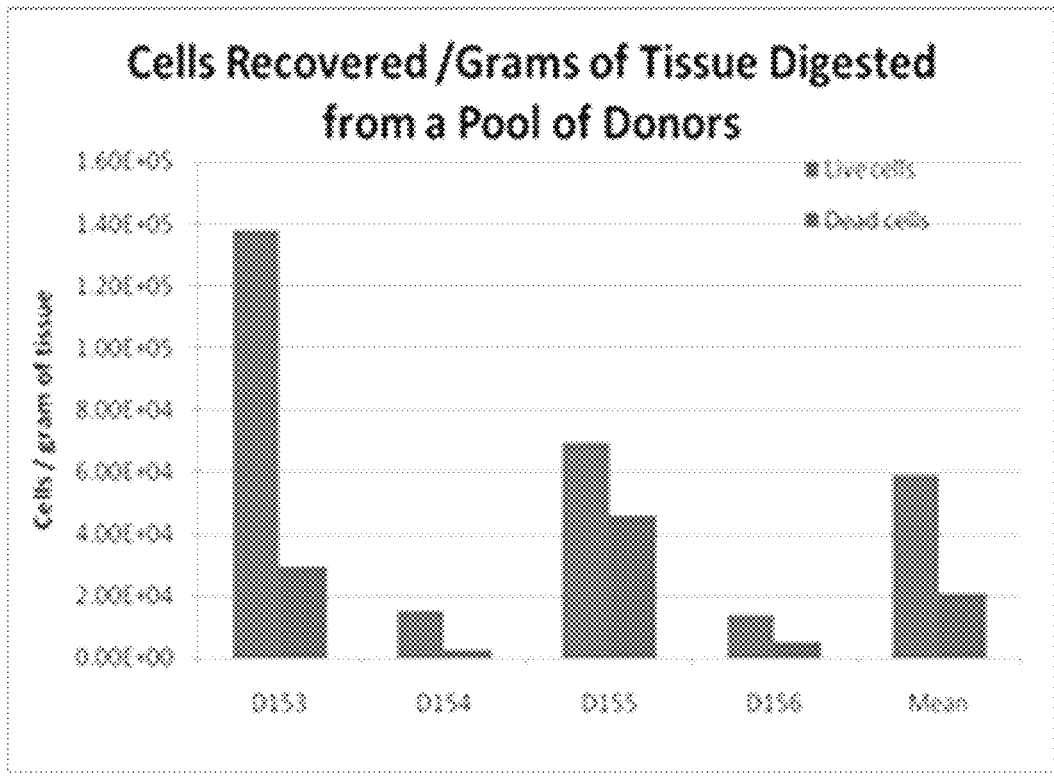
FIG. 4 depicts recovery of viable cells isolated by digestion.

As depicted in FIG. 4, digestion of an intact membrane as taught herein produces a surprising number of cells, and does so without mechanical disruption of the membrane. Also depicted in FIG. 4, digestion of a membrane as taught herein produces a surprisingly high ratio of viable to nonviable cells.

As depicted in FIG. 1, a fresh placental product of the present invention comprises surprisingly high cell viability. Also as depicted in FIG. 1, a placental product of the present invention subjected to a freeze-thaw cycle comprises surprisingly high cell viability. Also as depicted in FIG. 1, a placental product of the present invention, cell viability is retained surprisingly well after a freeze-thaw cycle.

Example 9 Isolation of Placental Cells

Figure 5:
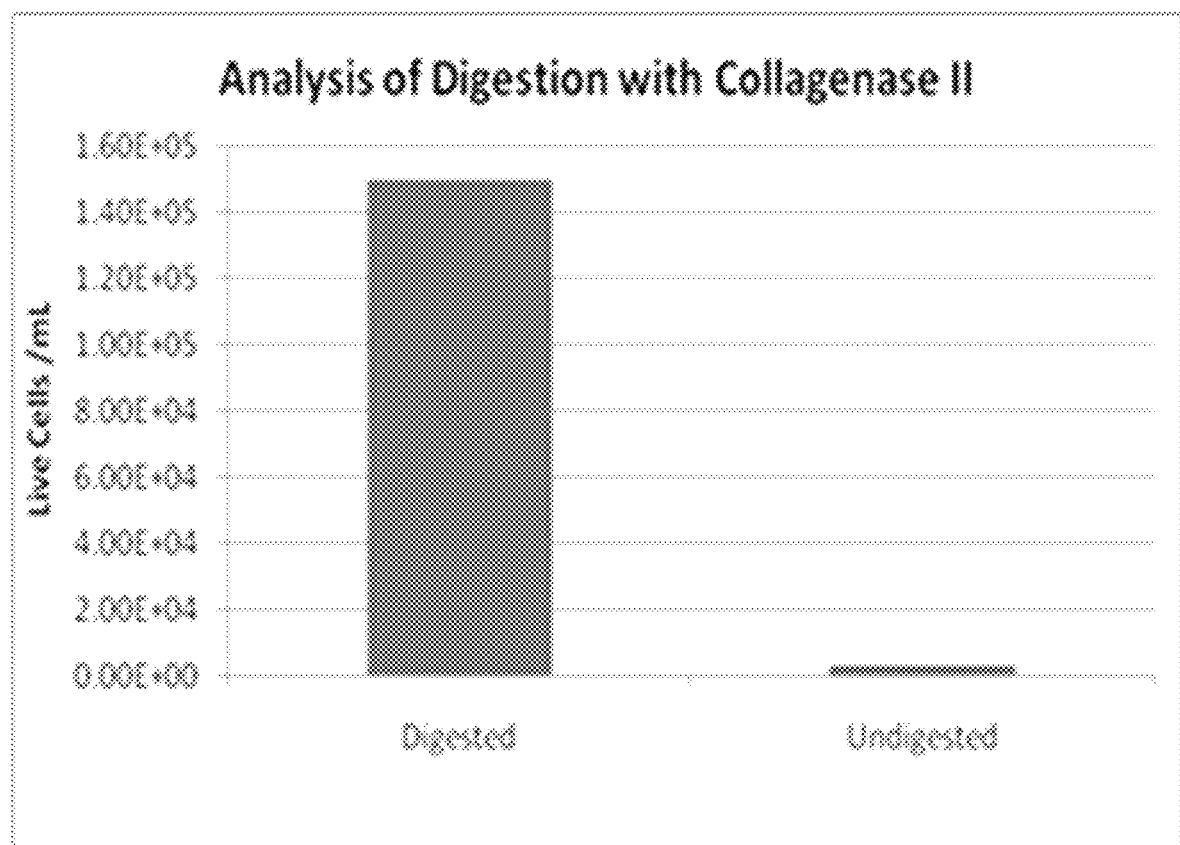
FIG. 5 depicts the level of viable cells in a placental product made with or without a step of cell isolation before tissue disruption.

Manufacturing methods were explored to obtain superior recovery of live cells in the placental dispersion. Specifically, an experiment was performed to determine the level of viable cells in a placental product manufactured with or without a step of cell isolation before homogenization. Briefly, a placenta prepared according to the procedure detailed in Example 1. The resulting chorion membrane was then divided into equal halves. Half the tissue was processed as described in Example 2 through Example 5 and the other half was processed in the same manner but without cell isolation (collagenase II digestion) prior to homogenization followed by recombining the isolated cells with the dispersion. Cells were counted using a hemocytometer and trypan blue staining was used to distinguish live cells. The data are presented in FIG. 5.

Results indicate that without prior digestion, homogenization eliminates virtually all viable cells from the end dispersion. Surprisingly, a placental product contains a substantially greater number of viable cells and is provides enhanced therapeutic efficacy when manufactured with a step of cell isolation before homogenization.

Example 10 Profile of a Placental Product

Multiple placental products were prepared, each from a different donor, according to the procedure detailed in Example 1 through Example 6 and placental factors were analyzed. Briefly, 1 mL of homogenate from each placental product was centrifuged at 14,000 rpm in a microcentrifuge for 10 min.

The resulting supernatant from each sample was collected as a test sample. Negative control samples consisted of 5% DMSO in saline (cryopreservation solution) and positive control samples consisted of cryopreservation solution with a known concentration of spiked recombinant proteins (bFGF, EGF, and VEGF). Protein profiles comprising placental factors listed in Table 1 were obtained using the SearchLight protein array assay (Aushon Biosystems). Results are indicated in Table 1 as a minimum and maximum expression levels (pg/mL) in a pool of four donors. Since the supernatant is analyzed rather than the complete homogenate, it is likely that protein level estimates are below actual concentrations in each chorion membrane homogenate containing live cells. The levels of VEGF and bFGF in each sample were confirmed by ELISA.

Surprisingly, many placental factors were detectable at levels that are known to be influential for burn wound healing as well as in the treatment of other indications.

As seen from the data in Table 1, placental products of the present invention comprise a therapeutic profile of placental factors.

Table 2 sets forth a therapeutic profile of placental products. Only now, with the teaching herein, the skilled artisan can examine the placental factors, consider the functional role as set forth in Table 3, and assess the value of a placental factor in wound repair.

TABLE 1

Therapeutic Profile of Factors in the Placental Products

| Protein | Min. (pg/mL) | Max. (pg/mL) | Mean (pg/mL) | Function |
|---|---|---|---|---|
| MMP1 | 2210.07 | 3468.94 | 2808.12 | Matrix and growth factor degradation, facilitate cell migration |
| MMP2 | 8207.46 | 70964.65 | 25648.74 | |
| MMP3 | 241.76 | 615.23 | 454.49 | |
| MMP7 | 79.78 | 4429.02 | 1190.31 | |
| MMP8 | 778.03 | 4661.35 | 2821.20 | |
| MMP9 | 32879.10 | 149579.10 | 71487.03 | |
| MMP10 | 6728.94 | 22686.00 | 14688.40 | |
| MMP13 | TLTD | TLTD | TLTD | |
| TIMP1 | 18739.41 | 315870.30 | 116341.69 | Inhibit activity of MMPs, angiogenic |
| TIMP2 | 7160.87 | 60711.15 | 21335.46 | |
| TSP1 | TLTD | TLTD | TLTD | Regulate TGFβ activity, anti-angiogenic |
| TSP2 | 1123.02 | 18784.67 | 6190.03 | |
| TGFα | TLTD | TLTD | TLTD | Stimulate growth and migration |
| TGFβ1 | 1041.50 | 6572.83 | 2661.65 | Promote angiogenesis, also proliferative and migration stimulatory effects |
| TGFβ2 | 91.81 | 1809.81 | 558.53 | |
| TGFβ3 | 77.02 | 146.31 | 104.35 | Promote angiogenesis, also proliferative and migration stimulatory effects Inhibit scar formation |
| bFGF (FGF-2) | 3554.58 | 11856.91 | 7479.40 | Promote angiogenesis, also proliferative and migration stimulatory effects |
| KGF (FGF-7) | 14.15 | 111.58 | 45.72 | Stimulate cell growth and migration |
| EGF | 0.42 | 3.72 | 1.57 | Stimulate cell growth and migration |
| HB-EGF | TLTD | TLTD | TLTD | |
| PDGFAA | 39.20 | 173.52 | 77.46 | Promote angiogenesis, also proliferative and migration stimulatory effects |
| PDGFAB | 495.90 | 495.90 | 495.90 | |
| PDGFBB | 7.73 | 235.85 | 70.56 | |
| VEGF | 13.95 | 211.17 | 76.73 | Promote angiogenesis, also proliferative and migration stimulatory effects |
| VEGFC | 64.77 | 178.51 | 118.71 | |
| VEGFD | 64.73 | 85.55 | 77.34 | |
| HGF | 9180.77 | 71280.10 | 27480.10 | Inhibit scar formation, stimulate cell growth and migration |
| PEDF | 805.18 | 805.18 | 805.18 | Stimulate growth and migration |
| ANG2 | TLTD | TLTD | TLTD | Stimulate growth and migration |
| IGFBP1 | 5022.96 | 1227128.50 | 322596.69 | Regulate IGF and its proliferative effects |
| IGFBP2 | 564.62 | 564.62 | 564.62 | |
| IGFBP3 | 226.20 | 809.16 | 603.93 | |
| ACRP30 | 6403.34 | 33898.70 | 16229.15 | Regulate growth and activity of keratinocytes |
| Fibronectin | 2950999.50 | 90198200.00 | 24973399.00 | ECM, cellular adhesion, stimulates growth and migration |
| Alpha2mae | 280783.30 | 4653881.00 | 1554151.49 | Inhibit protease activity, coordinate growth factor bioavailability |
| IL1ra | 961.93 | 10035.52 | 3568.27 | Anti-inflammatory |
| NGAL | 420.82 | 2908.38 | 1592.17 | Anti-bacterial |
| SDF1b | TLTD | TLTD | TLTD | Recruit cells from circulation to site of tissue damage |

TLTD = too low to detect

TABLE 2

Therapeutic Profile of Factors in the Chorionic Membrane

| Protein | Min. (pg/mL) | Max. (pg/mL) | Mean (pg/mL) |
|---|---|---|---|
| MMP1 | 2882.87 | 6582.26 | 4732.56 |
| MMP2 | 748.82 | 949.52 | 849.17 |
| MMP3 | TLTD | TLTD | TLTD |
| MMP7 | 4.46 | 9.07 | 6.76 |

TABLE 2-continued

Therapeutic Profile of Factors in the Chorionic Membrane

| Protein | Min. (pg/mL) | Max. (pg/mL) | Mean (pg/mL) |
|---|---|---|---|
| MMP8 | TLTD | TLTD | TLTD |
| MMP9 | 1259.30 | 2676.23 | 1967.77 |
| MMP10 | 79.31 | 87.51 | 83.41 |
| MMP13 | TLTD | TLTD | TLTD |
| TIMP1 | 17419.86 | 50712.30 | 34066.08 |
| TIMP2 | 640.73 | 779.98 | 710.36 |
| TGFα | TLTD | TLTD | TLTD |
| bFGF (FGF-2) | 351.28 | 375.05 | 363.17 |
| KGF (FGF-7) | 1.53 | 3.07 | 2.30 |
| EGF | 0.75 | 0.75 | 0.75 |
| HB-EGF | 15.40 | 84.49 | 49.94 |
| PDGFAA | 35.25 | 39.79 | 37.52 |
| PDGFAB | 14.03 | 14.43 | 14.23 |
| PDGFBB | 1.29 | 3.99 | 2.64 |
| VEGF | 8.39 | 125.16 | 66.78 |
| VEGFC | 51.74 | 123.45 | 87.60 |
| VEGFD | 14.99 | 20.42 | 17.70 |
| HGF | 29979.57 | 50392.75 | 40186.16 |
| PEDF | TLTD | TLTD | TLTD |
| ANG-2 | TLTD | TLTD | TLTD |
| IGFBP1 | 934.03 | 1443.63 | 1188.83 |
| IGFBR2 | 134.61 | 135.86 | 135.24 |
| IGFBP3 | 4571.51 | 11970.15 | 8270.83 |
| LIF | TLTD | TLTD | TLTD |
| GCSF | 0.74 | 1.22 | 0.98 |
| TPO | TLTD | TLTD | TLTD |
| PIGF | TLTD | TLTD | TLTD |
| ACRP30 | 225.35 | 1213.70 | 719.52 |
| Alpha2mac | 8174.44 | 9968.59 | 9071.52 |
| IL1a | 525.53 | 5168.21 | 2846.87 |
| NGAL | 229.72 | 938.51 | 584.11 |
| SDF1b | TLTD | TLTD | TLTD |

TLTD = too low to detect

TABLE 3

Functions of Placental Factors

| Specific Proteins | Selected Functions |
|---|---|
| Matrix Metalloproteinase 1 (MMP1), MMP2, 3, 7, 8, 9, 10, 13 | Matrix and growth factor degradation, facilitate cell migration |
| Tissue Inhibitors of MMPs (TIMP1 and TIMP2) | Inhibit activity of MMPs, angiogenic |
| Angiotensin-2 (Ang-2), Heparin-Bound Epidermal Growth Factor (HB-EGF), EGF, FGF-7 (also known as Keratinocyte Growth Factor-KGF), Placenta Growth Factor (PlGF), Pigment Epithelium Derived Factor (PEDF), Thrombopoietin (TPO), Transforming Growth Factor-α (TGF-α) | Stimulate growth and migration |
| Basic Fibroblast Growth Factor basic (bFGF), Platelet Derived Growth Factors (PDGF) AA, AB and BB, Vascular Endothelial Growth Factor (VEGF), VEGF-C and VEGF-D | Promote angiogenesis, also proliferative and migration stimulatory effects |
| TGF-β3, Hepatocyte Growth Factor (HGF) | Inhibit scar formation |
| α2-macroglobulin | Inhibit protease activity, coordinate growth factor bioavailability |
| Adiponectin (Acrp-30) | Regulate growth and activity of keratinocytes |
| Granulocyte Colony-Stimulating Factor (G-CSF) | Stimulate stem cell migration and proliferation |
| Interleukin 1 Receptor Antagonist (IL-1RA) | Anti-inflammatory |
| Neutrophil Gelatinase-Associated Lipocalin (N-GAL) | Anti-bacterial |
| Leukemia Inhibitory Factor (LIF) | Support of angiogenic growth factors |
| SDF-1β | Recruit cells from circulation to site of tissue damage |
| Insulin-like Growth Factor Binding Protein (IGFBP1, 2, 3) | Regulate IGF and its proliferative effects |

Example 11 Cell Phenotype

FACS was performed to determine cell phenotype in a placental product of the present invention. Placental products were prepared according to the procedure detailed in Example 1 through Example 6. The products were thawed and subsequently filtered through a 100 μm filter to remove tissue debris. Single cell suspensions were then centrifuged using a Beckman TJ-6 at 2000 rpm for 10 min and washed twice with DPBS. Supernatant was discarded after each wash, and cells were resuspended in 2 mL of FACS staining buffer (DPBS+0.09% $NaN_3$+1% FBS).

Figure 6:
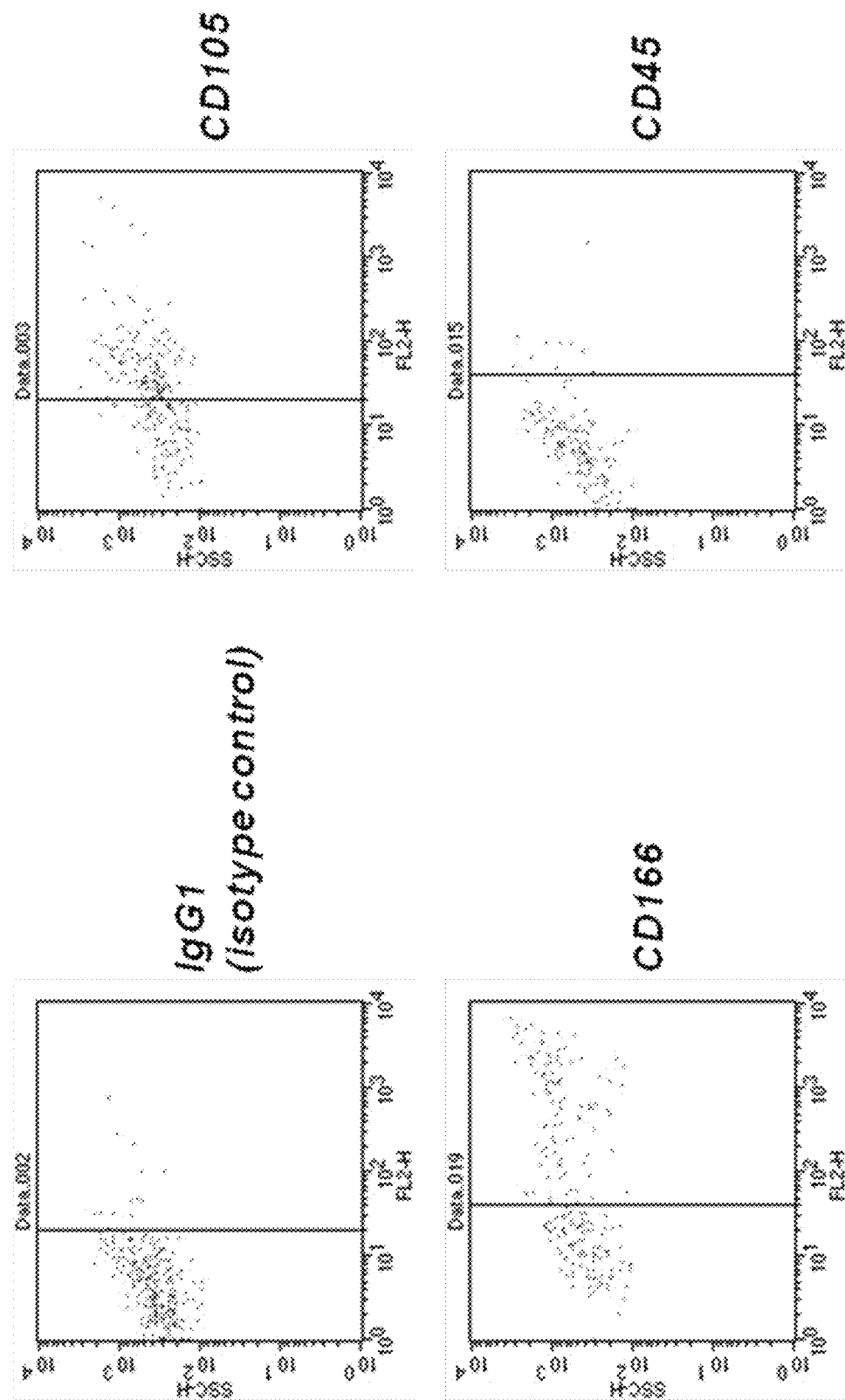
FIG. 6 depicts cell phenotype of cells in a placental product.

Once the single cell suspensions were prepared, a minimum of $1 \times 10^5$ cells in 100 μL of FACS staining buffer was treated with antibodies labeled with fluorescent dye. Table 4 provides descriptions of the antibodies and the amounts used. For cell surface markers, cells were incubated for 30 min at room temperature in the dark with antibodies followed by washing twice with FACS staining buffer by centrifugation at 1300 rpm for 5 min using a Beckman TJ-6 centrifuge. Cells were then resuspended in 400 μL of FACS staining buffer and analyzed using a BD FACSCalibur flow cytometer. Results indicate that a placental product derived from chorion contains live cells which stain positive for MSC markers (FIG. 6), implicating the presence of MSC-like cells.

TABLE 4

FACS Antibodies

| Cell marker antibody and label type | Cat No. | Volume of antibody solution used | Cell marker type | Cell marker specificity |
|---|---|---|---|---|
| IgG1 isotype-PE | BD 559320 | 5 μL | Cell surface | Isotype control |
| CD105-PE | Caltag MHCD10504 | 20 μL | Cell surface | MSC marker |
| CD166-PE | BD 559263 | 80 μL | Cell surface | MSC marker |
| CD45-PE | BD 555483 | 10 μL | Cell surface | Hematopoetic cell marker |

Example 12 Optimization of Cryoprotectants

Figure 7:
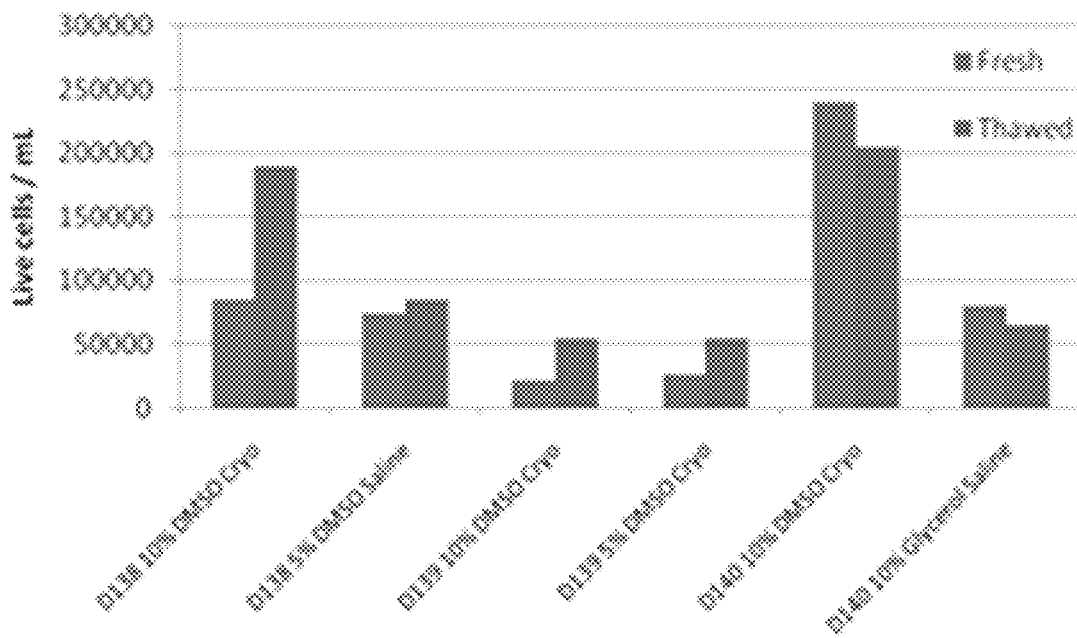
FIG. 7 depicts cell viability using various cryoprotectants

A placenta was processed according to the procedure detailed in Example 1 through Example 2. The resulting digestion suspension comprising cells was divided into several aliquots, and each processed according to the procedure detailed in Example 3 through Example 5 using a different cryoprotectant. Three different cryoprotectants were analyzed for their ability to enhance the number of viable cells recovered after freezing and to preserve protein recovery after freezing. The following cryoprotectant solutions were tested:
1. 10% DMSO and 5% HSA in Plasma-Lyte A (CTR solution)
2. 5% DMSO and 5% HSA in Plasma-Lyte A
3. 10% DMSO in Saline
4. 5% DMSO in Saline
5. 10% Glycerol in Saline Before freezing and after thawing, cells were counted using a hemocytometer and trypan blue staining was used to distinguish live cells. The following formula was used to calculate the number of cells per mL of homogenate: Cells per ml=(# Cells counted per four 0.0001 mL squares)×10,000× dilution factor. The results are depicted in FIG. 7.

Example 13 Time Course Optimization of Collagenase Digestion of Chorionic Tissue To determine the optimal time to digest a placental tissue such as chorionic tissues in collagenase II, chorionic tissues from three different donors were analyzed. The tissues were incubated overnight in an antibiotic cocktail. Each chorionic membrane tissue was then washed twice to remove antibiotic solution and split into three pieces. Each piece of tissue was weighed to obtain an initial weight (0 min.) before being digested for 10, 20, or 30 minutes in collagenase II solution (300 U/mL).

At the end of each digestion period, the remaining tissue was separated from the collagenase II solution containing the isolated cells by filtering through a 100 um pore cell filter. The separated tissue was then weighed while the collagenase II solution containing digested cells was centrifuged. The resulting cell pellet was resuspended in PBS and counted using a hemocytometer with trypan blue exclusion.

The weight of each remaining tissue piece, including the weight of tissue remaining on the cell filter, was used to calculate the percent of weight lost by digestion with collagenase II.

Figure 8:
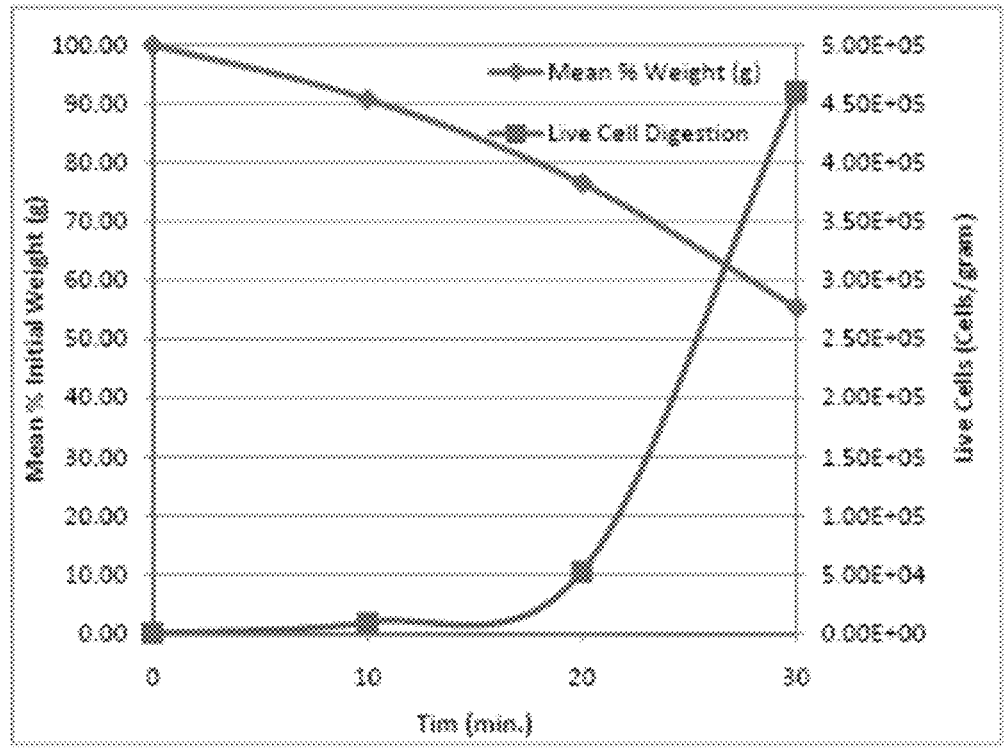
FIG. 8 depicts placental tissue weight and live cells recovered following collagenase treatment of various incubation times.

As shown in FIG. 8, after 10 min. of digestion, about 10% of the original tissue weight was reduced. Further incubation resulted in a more dramatic loss of weight. By 30 minutes, nearly half of the original weight was lost. It was further noted that tissue digested for longer than 10 min. became extremely difficult to separate from the collagenase II solution.

FIG. 8 also shows the number of cells released by collagenase digestion. After 10 minutes of incubation, a substantial number of cells were released. However, by 20 minutes, the number of cells released increased by about 4-fold.

These results surprising demonstrate that by performing only a limited collagenase digestion (e.g. about 10 minutes), a substantial number of placental cells can be released and the integrity of the placental tissue is maintained. Accordingly, when the limited collagenase digested placental tissue is subsequently disrupted, the dispersion retains a substantial amount of its native character. For example, the inventors generally observe that after prolonged collagenase digestion (e.g. 30 minutes), the placental tissue can be passed through a 100 micron filter. This is in contrast to the limited digestion where substantially less (e.g. one half or one quarter or less) of the tissue can be passed through a 100 micron filter.

When this dispersion is combined with the released placental cells, a superior therapeutic product is produced.

In data not shown, no significant change in the viability of the collagenase-released cells was observed through 30 min. of digestion.

Example 14 Time Course Optimization of Collagenase Digestion of Amniotic Tissue The limited digestion method of Example 13 was tested for applicability when the placental tissue is amniotic tissue. The following procedure was performed:
1. Process placenta.
  a. Remove amniotic tissue and wash twice in PBS.
  b. Soak amniotic tissue to loosen red blood cells.
    i. If needed, clear red blood cells from tissue using fingers.

c. Incubate amniotic tissue for 24 hrs. in antibiotic cocktail.
2. Remove amniotic tissue from antibiotic cocktail and wash twice in PBS.
3. Incubate amniotic tissue for 30 min at 37° C. in 200 mL trypsin solution (0.25%).
4. Remove amniotic tissue from trypsin solution and wash twice in PBS.
5. Incubate amniotic tissue for 10 min at 37° C. in 200 mL collagenase II solution (300 U/mL in DMEM).
6. Remove amniotic tissue from collagenase II solution and wash twice in PBS.
7. Processing of collagenase II and trypsin live cell suspensions.
   a. Centrifuge each suspension at 2000 rcf for 5 min.
   b. Pour off each supernatant and replace with 10 mL PBS.
      i. Resuspend cells in PBS to wash.
   c. Centrifuge cell suspension at 2000 rcf for 5 min.
   d. Pour off supernatants and resuspend cells in 2 mL cryprotectant (5% DMSO in saline).
   e. Combine pellets.
8. Processing of amniotic tissue.
   a. Place amniotic tissue in homogenization container with a volume of cryoprotectant (mL) equal to the weight of the amniotic membrane (g). For example, if the amniotic membrane weight 25 g place it in the homogenization container with 25 mL of cryoprotectant.
   b. Allow the amniotic tissue and cryoprotectant to sit on ice for at least 10 min.
   c. Homogenize at high speed twice for 5 sec. using a tissue homogenizer.
9. Combine isolated live cells with homogenate and mix thoroughly (the "placental product").
10. Aliquot into vials and place at 4° C. for 30-60 min. Freeze at −80° C. until use.

To determine the mean number of live cells in the amnion homogenate, multiple placentas were prepared. Each amnion was processed in one piece, and cell counts were obtained post thaw after cryopreservation (incubation at 4° C. and subsequent freezing at −80° C.). All cell count data were pooled, and a mean was calculated.

Samples from each donor were also prepared for protein array analysis. Briefly, 1 mL of homogenate from each donor was centrifuged at 14,000 rpm in a microcentrifuge for 10 min. The resulting supernatant from each sample was collected. Supernatants along with positive and negative controls were sent to Aushon Biosystems for analysis using their SearchLight protein array assay. This assay measures the levels of 37 proteins of interest in each sample. For this experiment, negative control samples consisted of 5% DMSO in saline (cryopreservation solution), and positive control samples consisted of cryopreservation solution with known concentrations of spiked recombinant proteins (bFGF, EGF, and VEGF).

FACS analysis of single cell suspensions from the placental product was performed for the markers CD45, CD 105, and CD 166.

Results.

Figure 9:
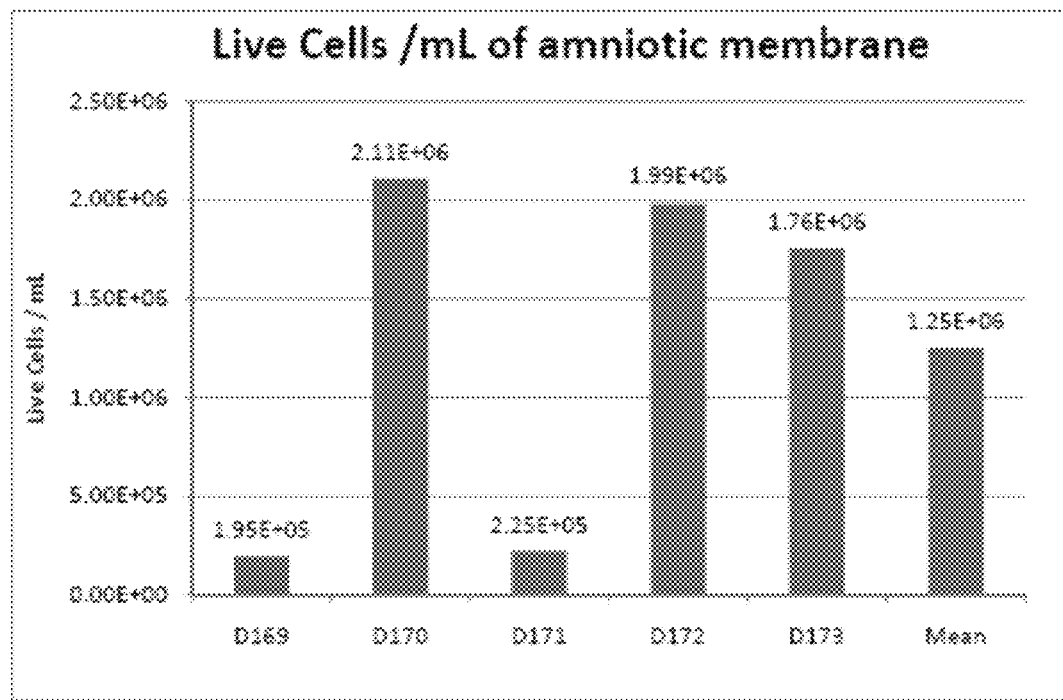
FIG. 9 depicts the number of collagenase-released cells from multiple donors.

As shown in FIG. 9, limited collagenase digestion of amniotic membrane tissue resulted in release of a substantial number of live placental cells.

As shown in Table 5, limited collagenase digestion of amniotic membrane tissue preserved placental factors in the placental dispersion made therefrom.

When Example 13 and Example 14 are considered together, it is now concluded that limited collagenase digestion of placental tissue, whether it be chorion tissue, amniotic tissue, or other tissue of placental origin, results unexpectedly in:

Substantial numbers of release live placental cells;
Preserved endogenous placental factors;
Preserved endogenous placental protein (e.g. matrix proteins); and
A therapeutically effective product.

TABLE 5

Therapeutic Profiles of Amnion-Derived Placental Products

| Protein | Min. (pg/mL) | Max. (pg/mL) | Mean (pg/mL) |
|---|---|---|---|
| MMP1 | 6697.73 | 10010.27 | 8354 |
| MMP2 | 5456.52 | 53432.45 | 29444.49 |
| MMP3 | 570.97 | 579.1 | 575.04 |
| MMP7 | 74.11 | 207.31 | 140.71 |
| MMP8 | 3829.63 | 3978.42 | 3904.03 |
| MMP9 | 11735.19 | 43661.63 | 27698.41 |
| MMP10 | 38916.81 | 51526.9 | 45221.86 |
| MMP13 | TLTD | TLTD | TLTD |
| TIMP1 | 31427.94 | 78147 | 54787.47 |
| TIMP2 | 6149.25 | 23167.29 | 14658.27 |
| TSP1 | TLTD | TLTD | TLTD |
| TSP2 | 7741.98 | 13312.64 | 10527.31 |
| TGFα | TLTD | TLTD | TLTD |
| TGFβ1 | 85.17 | 350.51 | 217.84 |
| TGFβ2 | 47.98 | 58.6 | 53.29 |
| bFGF (FGF-2) | 19305.72 | 23427.48 | 21366.6 |
| KGF (FGF-7) | 70.39 | 94.29 | 82.34 |
| EGF | 13.71 | 69.55 | 41.63 |
| HB-FGF | TLTD | TLTD | TLTD |
| PDGFAA | 14.47 | 27.93 | 21.2 |
| PDGFAB | TLTD | TLTD | TLTD |
| PDGFBB | 7.49 | 12.34 | 9.91 |
| VEGF | 346.3 | 1058.85 | 702.57 |
| VEGFC | 114.35 | 220.27 | 167.31 |
| VEGFD | 49.54 | 75.29 | 62.42 |
| HGF | 12068.53 | 17408.53 | 14738.53 |
| PEDF | TLTD | TLTD | TLTD |
| ANG2 | TLTD | TLTD | TLTD |
| IGFBP1 | 128.6 | 159.84 | 144.22 |
| IGFBP2 | TLTD | TLTD | TLTD |
| IGFBP3 | 699.01 | 1349.06 | 1024.04 |
| ACRP30 | 6677.35 | 11232.13 | 8954.74 |
| Fibronectin | 141595.2 | 254184.05 | 197889.63 |
| Alpha2mac | 421402.95 | 790851 | 606126.98 |
| IL1ra | 7542.74 | 10535.55 | 9039.14 |
| NGAL | 1521.63 | 3283.59 | 2402.61 |
| SDF1b | TLTD | TLTD | TLTD |

TLTD = too low to detect

Example 15 Live Cells from the Placental Dispersions and the Placental Cell Components of the Placental Product The manufacturing steps taught here (e.g. limited collagenase digestion, removal of placental cells before placental tissue disruption, and limited disruption methods) result in a highly effective therapeutic product. The relative role of the placental dispersion and the placental cells components were evaluated for respective role in providing live cells.

Chorionic tissue was obtained from placental tissue of 9 subjects and the placental cells (e.g. collagenase-released) and placental dispersion was assessed for the number of live cells.

TABLE 6

Placental Cells from Placental Cell and Placental Dispersion Fractions

| Donor | Cells in the Placental cell fraction (collagenase-released) | Cells in the Placental dispersion fraction | Theoretical cells in the placental product |
|---|---|---|---|
| D144 | 3.84E+05 | 7.95E+06 | 8.33E+06 |
| D145 | 8.40E+05 | 1.25E+07 | 1.33E+07 |
| D146 | 1.60E+05 | 7.84E+06 | 8.00E+06 |
| D147 | 2.17E+07 | 5.70E+06 | 2.74E+07 |
| D153 | 3.26E+06 | 1.64E+07 | 1.97E+07 |
| D154 | 3.70E+05 | 1.07E+07 | 1.11E+07 |
| D155 | 2.08E+06 | 7.10E+06 | 9.18E+06 |
| D156 | 4.90E+05 | 1.26E+07 | 1.31E+07 |
| Mean | 3.66E+06 | 1.01E+07 | 1.38E+07 |

As shown in Table 6, 21% to 98% of the cells in the placental products were derived from the placental dispersion component. Thus, the methods of the present invention unexpectedly preserve important placental factors and live cells in the placental dispersion and also provide substantial numbers of live cells from the placental cell (collagenase-released) component.

Example 16 Hypoxia Treatment

Results from private studies indicate that hypoxia induces many proteins having beneficial functions in the process of burn wound healing. However, the extent to which hypoxia effects cell growth and protein expression depends on the specific conditions of its application. Therefore, several experiments were performed to determine if hypoxia could enhance the effectiveness of chorion-derived placental products.

Figure 10:
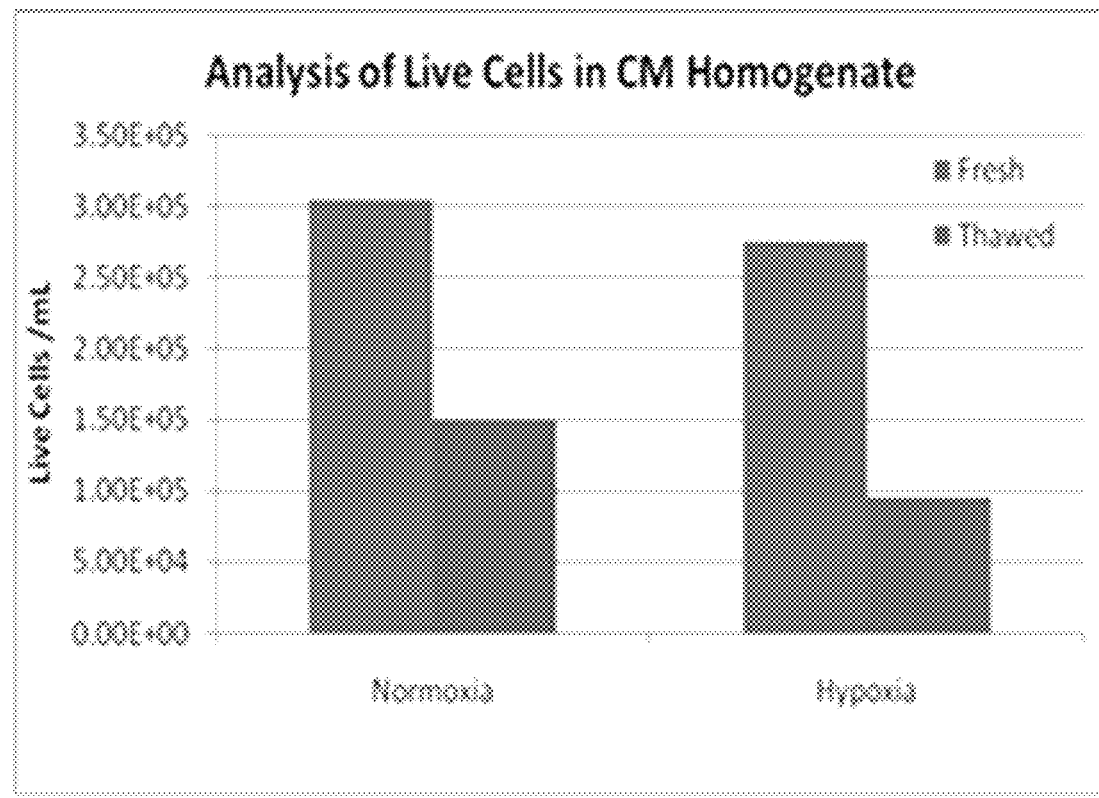
FIG. 10 depicts viable cell level in a placental product when a placenta is subjected to hypoxic or normoxic conditions.

A placenta was processed according to the procedure detailed in Example 1, except the chorionic membrane was divided into two halves before treatment with the antibiotic cocktail. One half of the chorionic membrane tissue was incubated under hypoxic conditions (1% O2) while the other was incubated under normal cell culture conditions (~20% O2). Each half was then process as described in Example 2 through Example 5. Before freezing and after thawing, cells were counted using a hemocytometer and trypan blue staining was used to distinguish live cells. The results are depicted in FIG. 10.

Example 17 Hypoxia Treatment and Cryoprotectants

Figure 11:
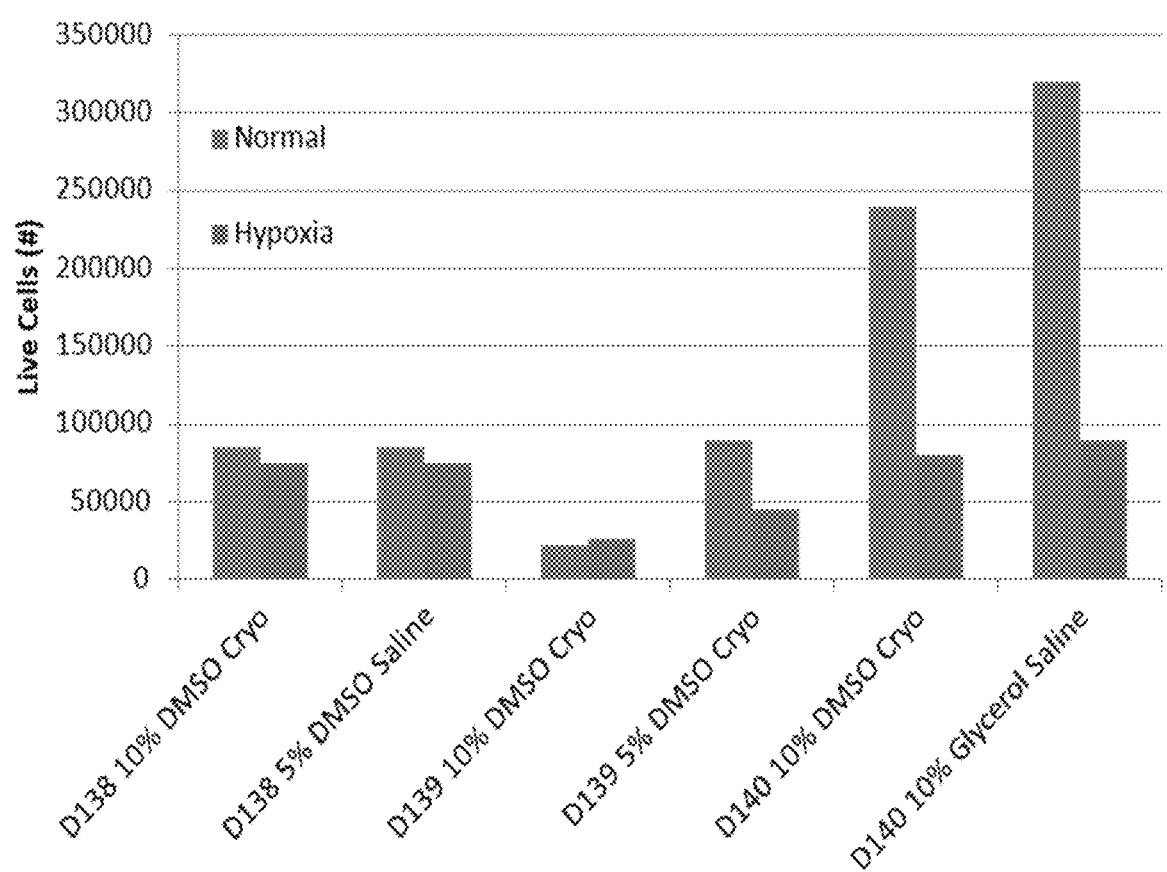
FIG. 11 depicts cell viability when a placenta is subjected to hypoxic or normoxic conditions.

A placenta was processed according to the procedure detailed in Example 15 except that the digests from each half of the chorionic membrane were further split and formulated with different cryoprotectants, as in Example 12. Before freezing and after thawing, cells were counted using a hemocytometer and trypan blue staining was used to distinguish live cells. The data are presented in FIG. 11. As depicted in FIG. 11, processing under normoxic conditions provides superior cell viability. Also as depicted in FIG. 11, subjecting the chorion to hypoxic conditions may be detrimental to cell viability.

Example 18 Growth Factors are Expressed for a Minimum of 14 Days

Placental products of the present invention demonstrate a durable effect, desirable for wound healing treatments. The extracellular matrix and presence of viable cells within the placental product derived from the chorionic membrane described in this invention allow for a cocktail of proteins that are known to be important for wound healing to be present for at least 14 days.

Figure 12A:
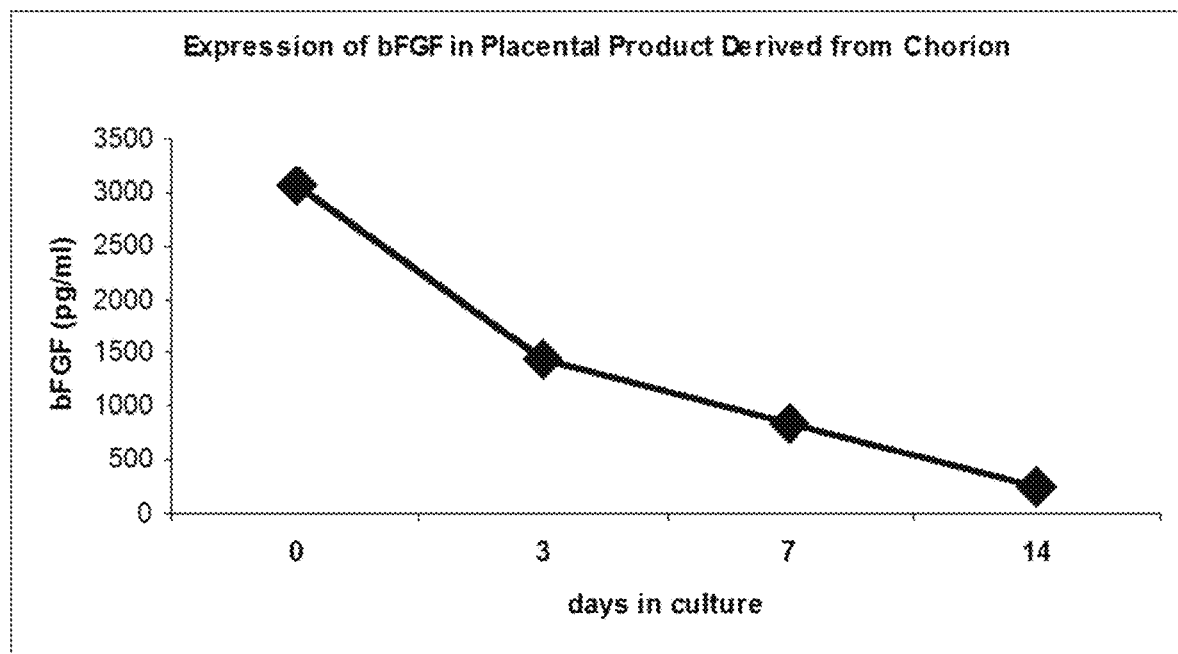
FIGS. 12A and 12B depict expression of bFGF (12A) and VEGF (12B) in placental products for 14 days in culture.
Figure 12B:
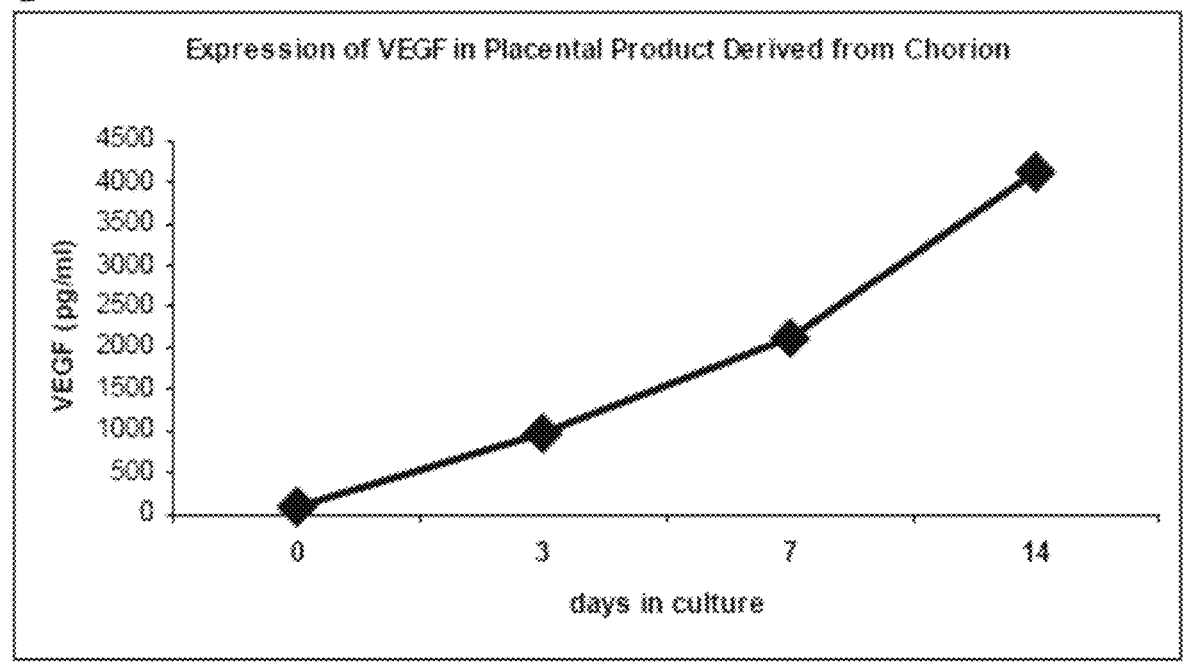

Placental product derived from the chorionic membrane were thawed and plated onto tissue culture wells and incubated at 37° C.±2° C. for 3, 7, and 14 days. At each time point, a sample of the product was collected and centrifuged at 16,000 g for 10 min to collect the supernatant. The supernatants were then run on ELISAs for bFGF and VEGF. FIG. 12 illustrates the duration of two key wound healing proteins, bFGF and VEGF, at 3, 7 and 14 days. Although the expression of bFGF goes down with time, it should be noted that significant levels of bFGF was present even out to 14 days. Interestingly, the expression of VEGF increased with time, which could be due to continued active expression of VEGF from the viable cells within the placental product derived from the chorionic membrane.

Example 19 Interferon 2α (IFN-2α) and Transforming Growth Factor-β3 (TGF-β3)

Figure 13A:
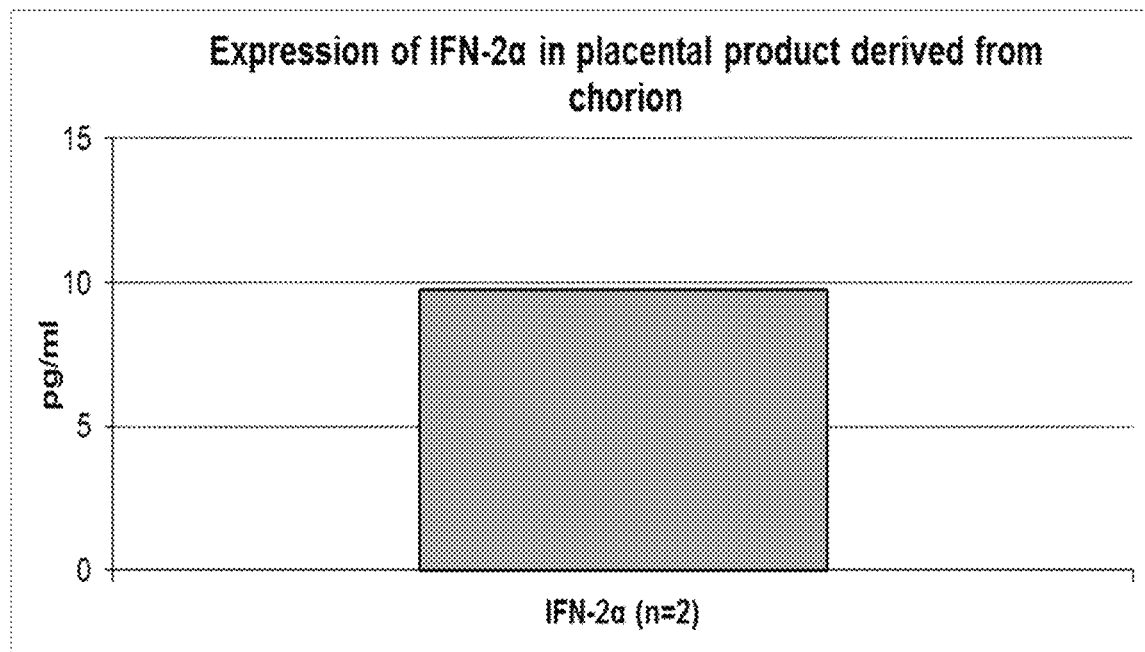
FIGS. 13A and 13B depict expression of IFN-2α (13A) and TGF-ß3 (13B) in placental products.
Figure 13B:
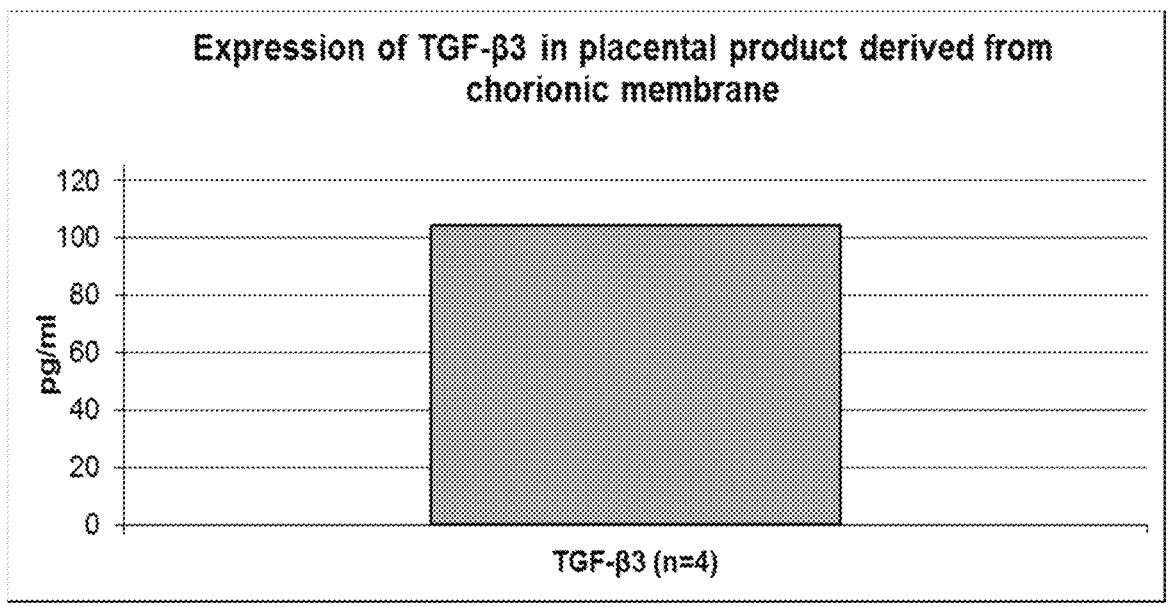

Interferon-2α and TGF-β3 have been described in the literature as playing critical roles in the prevention of scar and contracture formation (Kwan et al., Hand Clin, 2009, 25:511; Tredget et al., Surg Clin North Am 1997, 77:701). IFN-2α is known to decrease collagen and fibronectin synthesis and fibroblast-mediated wound contracture. Clinically, IFN-2α has been administered subcutaneously and shown to improve scar quality (Nedelec et al, Lab Clin Med 1995, 126:474). TGF-β3 regulates the deposition of extracellular matrix and has been shown to decrease scar formation when injected in rodent cutaneous wound models. Clinically, TGF-β3 has been shown to improve scar appearance when injected at the wound site (Occleston et al., J Biomater Sci Polym Ed 2008, 19:1047). Placental product derived from the chorionic membrane described in this invention has been analyzed for the presence of IFN-2α and TGF-β3. Briefly, placental product derived from the chorionic membrane was thawed and centrifuged at 16,000 g to collect supernatants. Supernatants were analyzed on a commercially available ELISA kit from MabTech (IFN-2α) and R&D Systems (TGF-β3). FIG. 13 shows significant expression of IFN-2α and TGF-β3 in placenta products derived from the chorionic membrane.

Example 20 Tissue Reparative Proteins in Chorionic Membrane Homogenates

Placental product derived from the chorionic membrane was analyzed for the presence of proteins that are important in tissue repair.

Figure 14A:
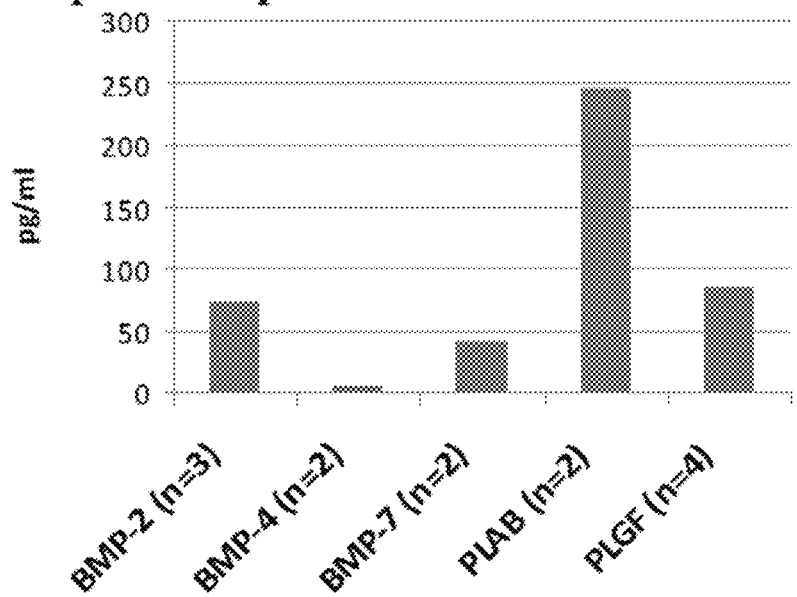
FIGS. 14A and 14B depict BMP-2, BMP-4, BMP-7, PLAB, and PLGF (14A), and IGF-1 (14B) expression in placental products derived from the chorionic membrane.
Figure 14B:
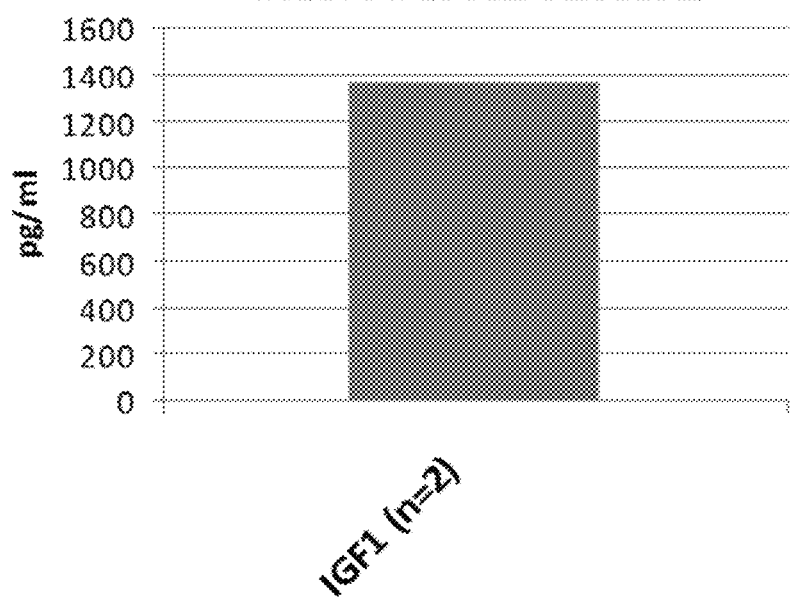

Placental products derived from chorionic membranes described in this invention were analyzed for the presence of these tissue reparative proteins. Briefly, placental product derived from the chorionic membrane was incubated at 37° C.±2° C. for 72 hrs. The product was centrifuged, and the supernatant was analyzed on commercially available ELISA kits from R&D Systems. FIG. 14 shows significant expression of BMP-2, BMP-4, BMP-7, PLAB, PlGF, and IGF-1 in several donors of placental products derived from chorionic membranes.

Without being bound by theory, the inventors believe that efficacy of the present placental products for wound repair are due, in part, to the role of BMPs, IGF-1, and PlGF in the development and homeostasis of various tissues by regulating key cellular processes. BMP-2 and BMP-4 may stimulate differentiation of MSCs to osteoblasts in addition to promote cell growth; placental BMP or PLAB is a novel member of the BMP family that is suggested to mediate embryonic development. Insulin-like growth factor 1 (IGF-1) may promotes proliferation and differentiation of osteoprogenitor cells. Placental derived growth factor (PlGF) may acts as a mitogen for osteoblasts.

Without being bound by theory, the inventors believe that efficacy of the present placental products for wound repair are due, in part, to the role of BMPs, IGF-1, and PlGF in the development and homeostasis of various tissues by regulating key cellular processes. BMP-2 and BMP-4 may stimulate differentiation of MSCs to osteoblasts in addition to promote cell growth; placental BMP or PLAB is a novel member of the BMP family that is suggested to mediate embryonic development. Insulin-like growth factor 1 (IGF-1) may promotes proliferation and differentiation of osteoprogenitor cells. Placental derived growth factor (PlGF) may acts as a mitogen for osteoblasts.

Example 21 Differentiation Capacity of Cells Derived from the Chorionic Membrane Placental cells, in optional embodiments of the present invention, are adherent, express specific cellular markers such as CD105 and lack expression of other markers such as CD45, and demonstrate the ability to differentiate into adipocytes, osteoblasts, and chondroblasts.

The expression of specific cellular markers has already been described in Example 20. To determine if the cells within the placental product derived from the chorionic membrane can adhere to plastic and differentiate into one of the lineages, cells were isolated from the placental product derived from the chorion as described in this invention and cultured at 37° C.±2° C. and expanded.

Figures 15A, 15B, 15C:
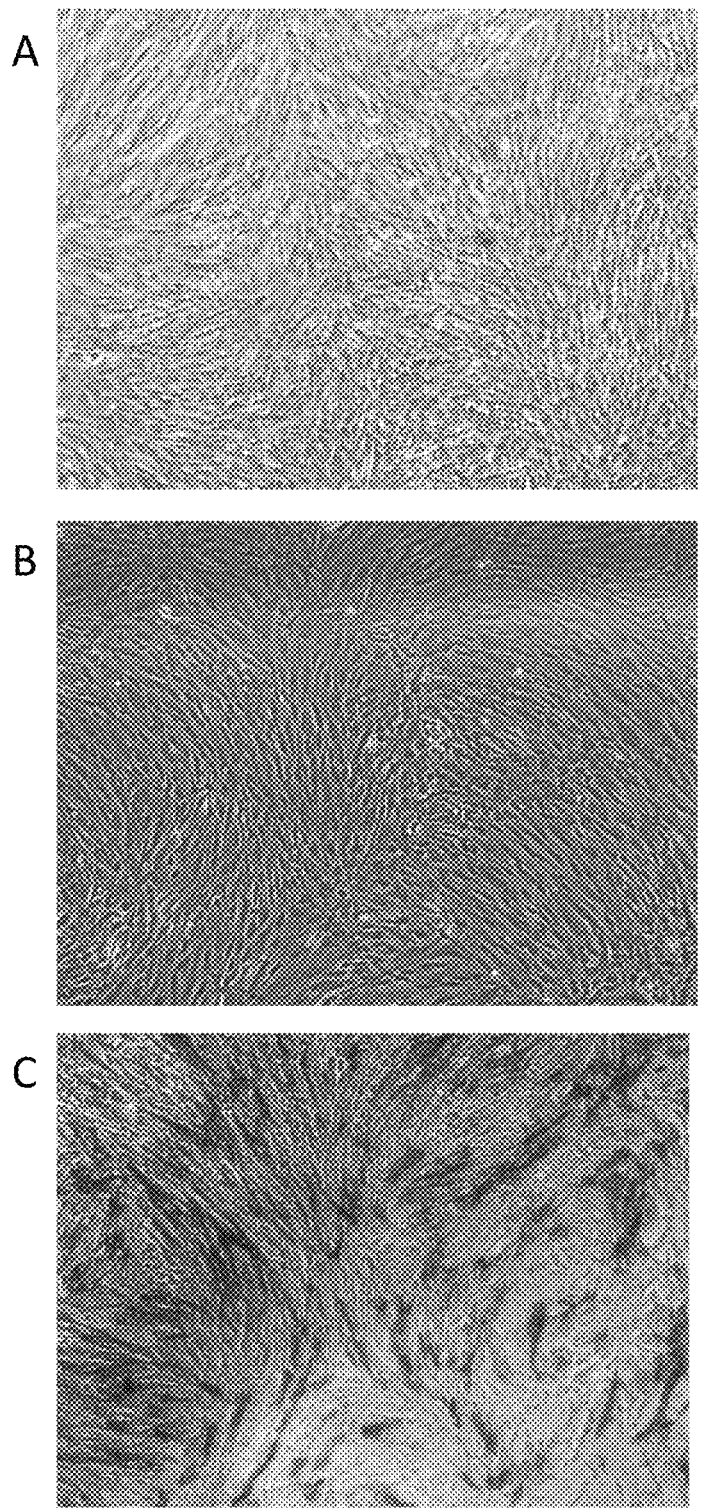
FIGS. 15A, 15B, and 15C show representative images of passage 2 cells isolated and expanded from a placental product derived from the chorionic membrane.
Figure 16:
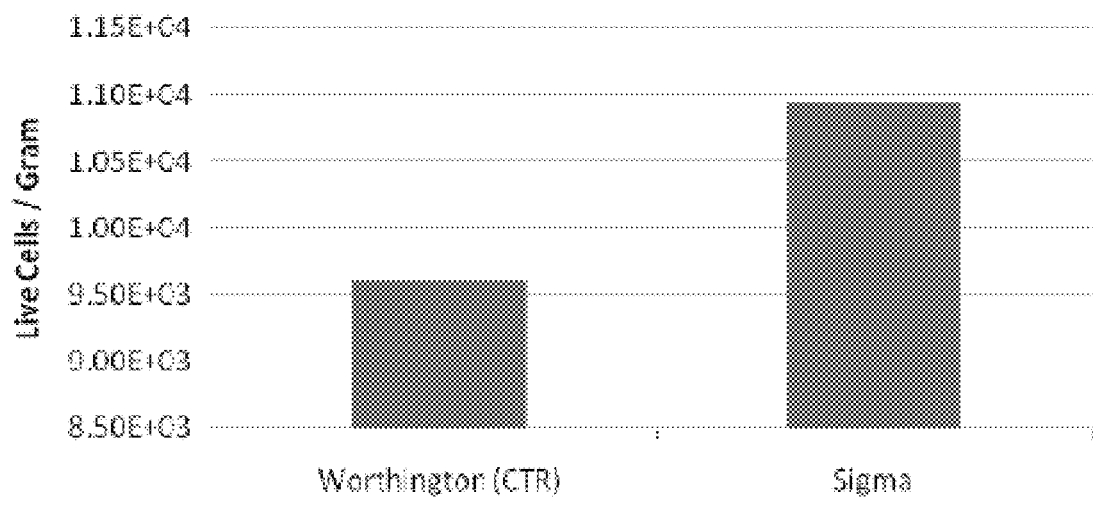
FIG. 16 depicts recovery of viable cells isolated by digestion using various collagenase II enzymes.
Figure 17:
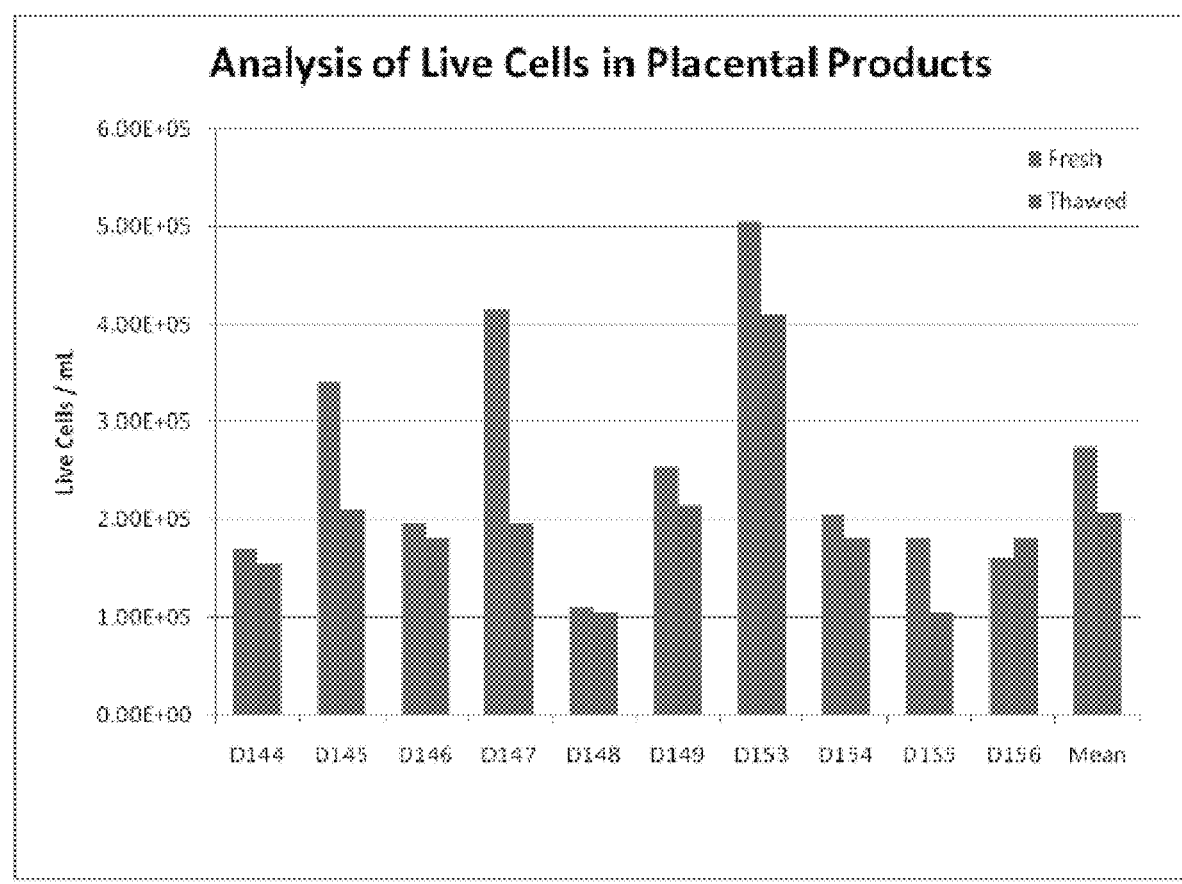
FIG. 17 depicts cell viability, before and after a freeze-thaw cycle of a placental product comprising isolated cells and a placental dispersion.

FIG. 15-A shows a representative image of passage 2 cells, demonstrating the ability of the cells to adhere to tissue culture plastic. As a comparison, a representative image of MSCs isolated and expanded from human bone marrow aspirate is shown in FIG. 15-B.

Osteogenic differentiation capacity was demonstrated by staining the cultured cells with alkaline phosphatase labeling following the manufacturer's recommendations (BCIP/NBT Alkaline Phosphatase Substrate Kit IV, Vector Laboratories Cat. No. SK-5400). Alkaline phosphatase is an enzyme involved in bone mineralization (Allori et al., Tissue Engineering: Part B, 2008, 8:275), and its expression within cells is indicative of osteo-precursor cells (Majors et al., J Orthopaedic Res, 1997, 15:546). Staining for alkaline phosphatase is carried out through an enzymatic reaction with Bromo-4-Chloro-3'-Indolylphosphate p-Toluidine Salt (BCIP) and Nitro-Blue Tetrazolium Chloride (NTP). BCIP is hydrolyzed by alkaline phosphatase to form an intermediate that undergoes dimerization to produce an indigo dye. The NBT is reduced to the NBT-formazan by the two reducing equivalents generated by the dimerization. Together these reactions produce an intense, insoluble black-purple precipitate when reacted with alkaline phosphatase.

FIG. 15-C shows a representative image of passage 2 cells isolated and expanded from placental product derived from the chorionic membrane staining positively for alkaline phosphatase.

What is claimed is:

1. A method of manufacturing a therapeutic placental product comprising:
   (a) obtaining a first placental tissue;
   (b) isolating placental cells from the first placental tissue;
   (c) obtaining a second placental tissue;
   (d) homogenizing the second placental tissue to form a homogenous placental dispersion comprising placental factors; and
   (e) combining the placental cells and the homogenous placental dispersion to form the placental product.

2. The method of claim 1, wherein the first placental tissue is autologous to the second placental tissue and wherein the first placental tissue and the second placental tissue are chorionic tissue.

3. The method of claim 2, wherein the second placental tissue is derived from the first placental tissue after the step of isolating the placental cells.

4. The method of claim 3, wherein the step of isolating the placental cells comprises exposing the first placental tissue to a protease, optionally wherein the protease is a collagenase.

5. The method of claim 4, wherein the protease exposing step has a duration of about 30 minutes or less.

6. The method of claim 4, wherein the protease exposing step releases less than about 10% of the maximum number of releasable placental cells.

7. The method of claim 2, wherein the chorionic tissue is depleted of trophoblasts.

8. The method of claim 7, wherein the trophoblasts are depleted by dissection and dispase treatment.

9. The method of claim 1, wherein the placental product comprises one or more members selected from the group consisting of extracellular matrix proteins; protease inhibitors; angiogenic factors; and placental factors which promotes the migration of epithelial cells into a wound.

10. The method of claim 1, wherein the placental product comprises one or more protease inhibitors selected from the group consisting of matrix metalloproteinases (TIMPs), alpha-2 macroglobulin, and thrombospondins.

11. The method of claim 1, wherein the placental product comprises one or more angiogenic factors selected from the group consisting of VEGF and bFGF.

12. The method of claim 1, wherein the placental product comprises one or more factors which promote the migration of epithelial cells into a wound selected from the group consisting of HGF and KGF.

13. The method of claim 1, wherein the placental cells are selected from the group consisting of MSCs, ESCs, placenta-derived mesenchymal progenitor cells, placental mesenchymal stem cells, fibroblasts, epithelial cells, placental mesenchymal cells, and macrophages.

14. The method of claim 13, wherein the placental cells are present at a concentration of at least about 20,000 per ml of placental product.

15. The method of claim 1, wherein at least one of the placental cells or the placental dispersion is cryopreserved.

16. The method of claim 1, wherein the placental cells are cryopreserved before combining with the placental dispersion, and wherein the placental dispersion is optionally cryopreserved before combining with the placental cells.

17. The method of claim 1, wherein the placental cells comprise stromal cells and the placental cells are cryopreserved.

18. The method of claim 3, wherein:
   (a) the step of isolating the placental cells comprises exposing the first placental tissue to a protease;
   (b) the protease exposing step is of about 30 minutes or less duration;

(c) the protease exposing step releases less than about 10% of the maximum number of releasable placental cells;
(d) the chorionic tissue is depleted of trophoblasts;
(e) the placental product comprises one or more protease inhibitors selected from the group consisting of matrix metalloproteinases (TIMPs), alpha-2 macroglobulin, and thrombospondins;
(f) the placental product comprises one or more of VEGF and bFGF;
(g) the placental product comprises one or more of HGF and KGF;
(h) the placental cells comprise MSCs and cells selected from the group consisting of ESCs, placenta-derived mesenchymal progenitor cells, placental mesenchymal stem cells, fibroblasts, epithelial cells, placental mesenchymal cells, and macrophages;
(i) the placental cells are present at a concentration of at least about 20,000 per ml of placental product; and
(j) at least one of the placental cells and the placental dispersion is cryopreserved.

19. A method of treating a tissue injury comprising administering to a subject in need thereof a therapeutic placental product made by the method of claim 1.

* * * * *